United States Patent
Apte et al.

(10) Patent No.: US 11,621,055 B2
(45) Date of Patent: Apr. 4, 2023

(54) MICROORGANISM-RELATED SIGNIFICANCE INDEX METRICS

(71) Applicant: PSOMAGEN, INC., Rockville, MD (US)

(72) Inventors: Zachary Apte, San Francisco, CA (US); Jessica Richman, San Francisco, CA (US); Daniel Almonacid, San Francisco, CA (US); Patricio Lagos, San Francisco, CA (US); Ricardo Castro, San Francisco, CA (US); Paz Tapia, San Francisco, CA (US)

(73) Assignee: Psomagen, Inc., Rockville, MD (US)

( * ) Notice: Subject to any disclaimer, the term of this patent is extended or adjusted under 35 U.S.C. 154(b) by 472 days.

(21) Appl. No.: 16/645,077

(22) PCT Filed: Sep. 14, 2018

(86) PCT No.: PCT/US2018/051222
§ 371 (c)(1),
(2) Date: Mar. 6, 2020

(87) PCT Pub. No.: WO2019/055874
PCT Pub. Date: Mar. 21, 2019

(65) Prior Publication Data
US 2020/0286623 A1   Sep. 10, 2020

Related U.S. Application Data

(60) Provisional application No. 62/558,489, filed on Sep. 14, 2017.

(51) Int. Cl.
*G16H 50/30* (2018.01)
*G16B 20/00* (2019.01)
(Continued)

(52) U.S. Cl.
CPC ............. *G16B 20/00* (2019.02); *C12Q 1/689* (2013.01); *G16H 50/20* (2018.01); *G16H 50/30* (2018.01);
(Continued)

(58) Field of Classification Search
CPC ........ G16B 20/00; G16H 50/30; G16H 50/20; C12Q 1/689; C12Q 2600/112; G01N 33/98
See application file for complete search history.

(56) References Cited

U.S. PATENT DOCUMENTS 7,206,699 B2 * 4/2007 Larder ................. C12Q 1/6876
702/22
10,480,037 B2 * 11/2019 Haddad .................. C12Q 1/703
(Continued)

FOREIGN PATENT DOCUMENTS

WO    2012050513 A1    4/2012
WO    2015112352 A1    7/2015
(Continued)

OTHER PUBLICATIONS

Dewhirst et al., "The Human Oral Microbiome," Journal of Bacteriology, vol. 192, No. 19, pp. 5002-5017, Oct. 1, 2010.
(Continued)

*Primary Examiner* — Gregory M Desire
(74) *Attorney, Agent, or Firm* — Morgan, Lewis & Bockius LLP

(57) ABSTRACT

Embodiments of a method and/or system, such as for characterizing at least one microorganism-related condition, can include: determining a set of associations (e.g., positive associations such as positive correlations, negative associations such as negative correlations, non-associations such as
(Continued)

no correlation or minimal correlation, etc.) between a set of microorganism taxa and at least one microorganism-related condition; determining a set of reference features (e.g., reference abundance ranges, etc.) for the set of microorganism taxa; and determining one or more significance index metrics based on the set of associations and the set of reference features.

23 Claims, 23 Drawing Sheets

(51) Int. Cl.
*G16H 50/20* (2018.01)
*C12Q 1/689* (2018.01)
*G01N 33/98* (2006.01)

(52) U.S. Cl.
CPC ........ *C12Q 2600/112* (2013.01); *G01N 33/98* (2013.01)

(56) References Cited

U.S. PATENT DOCUMENTS

| | | | |
|---|---|---|---|
| 11,015,154 B2* | 5/2021 | Justice | C12Q 1/689 |
| 11,227,667 B2* | 1/2022 | McNulty | G16B 50/30 |
| 2008/0318210 A1* | 12/2008 | Bentwich | C12Q 1/703 |
| | | | 435/6.16 |
| 2014/0335534 A1* | 11/2014 | Li | C12Q 1/6869 |
| | | | 435/6.15 |
| 2016/0224749 A1 | 8/2016 | Apte | |
| 2017/0329919 A1* | 11/2017 | Govro | G16H 40/20 |
| 2019/0080046 A1* | 3/2019 | Apte | G16B 20/00 |

FOREIGN PATENT DOCUMENTS

| | | | |
|---|---|---|---|
| WO | 2017044886 A1 | 3/2017 | |
| WO | 2017044901 A1 | 3/2017 | |

OTHER PUBLICATIONS

International Search Report and Written Opinion dated Nov. 12, 2018 in International Application No. PCT/US18/51222.

* cited by examiner

SmartJane™ Sample Report

Health Conditions of the Vaginal Microbiome

In the following pages you will find information about how your vaginal microbiome is involved in 10 different health conditions. When organisms in your microbiome are outside of the healthy range, the condition is more likely, based on scientific literature. Some organisms have a more significant impact on the condition than others. Where possible, all the results for each condition are summarized in the "Significance Index" where the impact of each organism is weighted. Below you find the Significance Index for 7 health conditions in 3 categories.

Significance Index

The Significance Index provides information about your results, summarizing all the microbial associations found with a given health condition into a single value. The Significance Index is calculated using healthy ranges that have been determined for each microorganism using a cohort of self-reported healthy individuals. Results include microorganisms selected from scientific literature that are both associated with and inversely associated with a health condition.

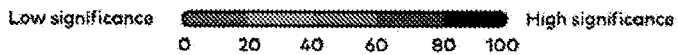

Low significance — High significance
0   20   40   60   80   100

The Significance Index is expressed as a numerical value from 0 to 100. A lower Significance Index indicates that your microbiome has a lower number of microorganisms outside the healthy range, while a higher Significance Index indicates that your microbiome has an increased number of microorganisms outside the healthy range.

The Significance Index does not predict the likelihood of developing a specific disease, nor does it imply protection against a specific disease. Detection of a microorganism by this test does not imply a diagnosis. Similarly, a lack of detection does not exclude the presence of a disease-causing microorganism or a diagnosis of disease. Please consult your healthcare provider to interpret the results provided in this report.

STI Associated Conditions

| Condition | Significance Index |
|---|---|
| Pelvic Inflammatory Disease | 33 |
| Infertility | 33 |

Vaginal Dysbiosis Associated Conditions

| Condition | Significance Index |
|---|---|
| Bacterial Vaginosis | 14 |
| Aerobic Vaginitis | 0 |

FIG. 8A

SmartJane™ Sample Report

STI Associated Conditions

The presence of certain microorganisms may cause active sexually transmitted infections (STIs), and may also be related to cervical inflammation (cervicitis), pelvic inflammation (pelvic inflammatory disease), and infertility. A positive result in your sample is not a diagnosis; similarly, a negative result does not rule out the possibility of disease. Please consult with a medical professional for follow up.

Sexually Transmitted Infection

| Association | Organism | Result | Out of Range |
|---|---|---|---|
| Associated | *Chlamydia trachomatis* [30-32] | ● Negative | |
| | *Mycoplasma genitalium* [33] | ● Positive | ⚠ Condition more likely |
| | *Neisseria gonorrhoeae* [34,35] | ● Negative | |
| | *Treponema pallidum* [36] | ● Negative | |

Cervicitis

| Association | Organism | Result | Out of Range |
|---|---|---|---|
| Associated | High-risk HPV [37] | ● Negative | |
| | *Chlamydia trachomatis* [38] | ● Negative | |
| | *Mycoplasma genitalium* [37] | ● Positive | ⚠ Condition more likely |
| Inversely associated | *Lactobacillus* [39] | ● Low | ⚠ Condition more likely |

Pelvic Inflammatory Disease     Significance Index 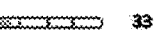 33

| Association | Organism | Result | Out of Range |
|---|---|---|---|
| Associated | *Chlamydia trachomatis* [40-42] | ● Negative | |
| | *Mycoplasma genitalium* [46,47] | ● Positive | ⚠ Condition more likely |
| | *Neisseria gonorrhoeae* [40,42-45] | ● Negative | |

Infertility     Significance Index 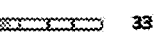 33

| Association | Organism | Result | Out of Range |
|---|---|---|---|
| Associated | *Chlamydia trachomatis* [40] | ● Negative | |
| | *Mycoplasma genitalium* [41] | ● Positive | ⚠ Condition more likely |
| | *Neisseria gonorrhoeae* [40] | ● Negative | |

FIG. 8B

SmartJane™ Sample Report

Vaginal Dysbiosis Associated Conditions

Vaginal dysbiosis is a term that describes an imbalance in the aerobic and anaerobic microorganisms normally present in your vagina. Vaginal dysbiosis may or may not have active clinical symptoms. Please consult with a medical professional for follow up regarding these results.

Bacterial Vaginosis — Significance Index: 14

| Association | Organism | Result | Out of Range |
|---|---|---|---|
| Associated | *Aerococcus* (48,49) | Normal | |
| | *Aerococcus christensenii* (50) | Normal | |
| | *Atopobium* (48,51) | Normal | |
| | *Atopobium vaginae* (49,50,52) | Normal | |
| | *Dialister microaerophilus* (50,53) | Normal | |
| | *Gardnerella* (48) | Normal | |
| | *Gardnerella vaginalis* (49-51,54) | Normal | |
| | *Gemella* (48,53) | Normal | |
| | *Megasphaera* (49-50) | Normal | |
| | *Mobiluncus curtisii* (55,56) | Normal | |
| | *Papillibacter* (49) | Normal | |
| | *Parvimonas* (48) | Normal | |
| | *Peptoniphilus* (48) | Normal | |
| | *Peptostreptococcus* (48,54) | Normal | |
| | *Porphyromonas* (48) | Normal | |
| | *Prevotella* (48-50,52,54) | Normal | |
| | *Prevotella amnii* (50,57) | Normal | |
| | *Prevotella timonensis* (50,53) | Normal | |
| | *Sneathia* (48,50) | Normal | |

FIG. 8C

SmartJane™ Sample Report

Vaginal Imbalance (continued)

| Bacterial Vaginosis (continued) | | Significance Index | |
|---|---|---|---|
| Association | Organism | Result | Out of Range |
| Inversely associated | Lactobacillus [49,50] | Low | Consider more Body |
| | Lactobacillus iners [48-50] | Low | Consider more Body |
| | Lactobacillus jensenii [48,50,58] | Low | Consider more Body |

| Aerobic Vaginitis | | Significance Index | 0 |
|---|---|---|---|
| Association | Organism | Result | Out of Range |
| Associated | Gardnerella vaginalis [59] | Normal | |
| | Staphylococcus aureus [59,60] | Normal | |
| | Streptococcus agalactiae [59] | Normal | |

FIG. 8D

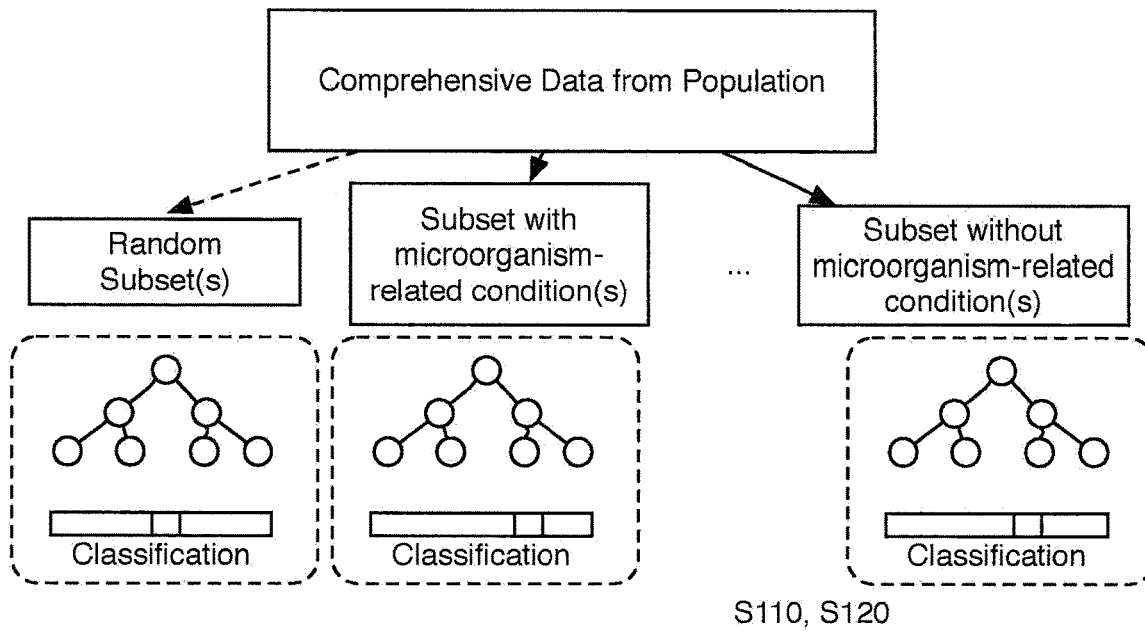
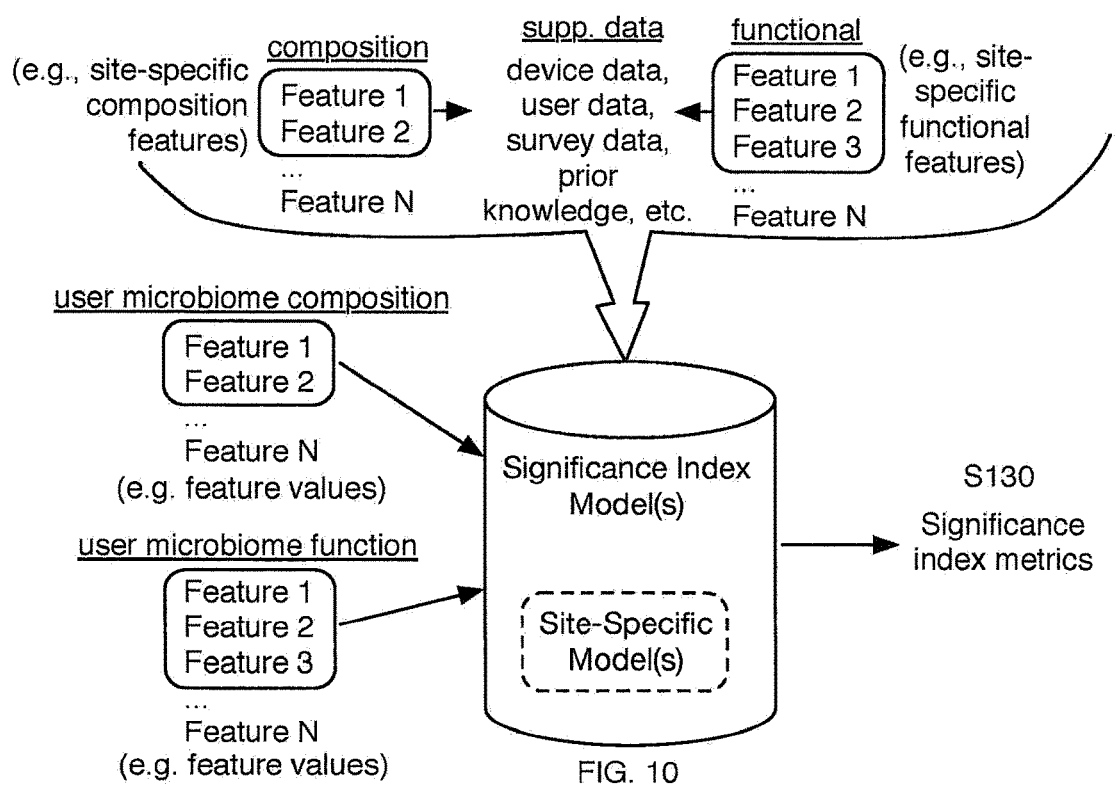
FIG. 10

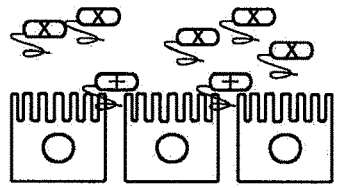
block pathogen entry
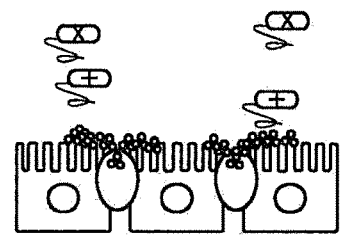
form mucous barrier
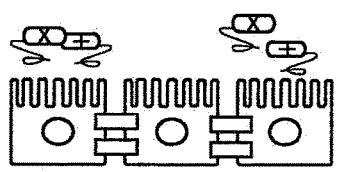
enhance apical tight junctions
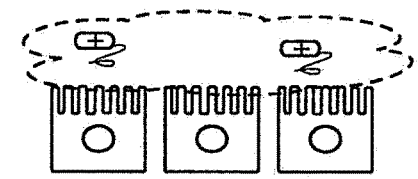
produce antimicrobial factors
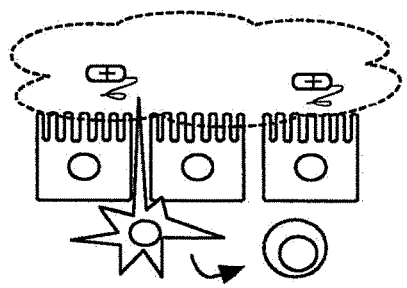
stimulate anti-inflammatory cytokines
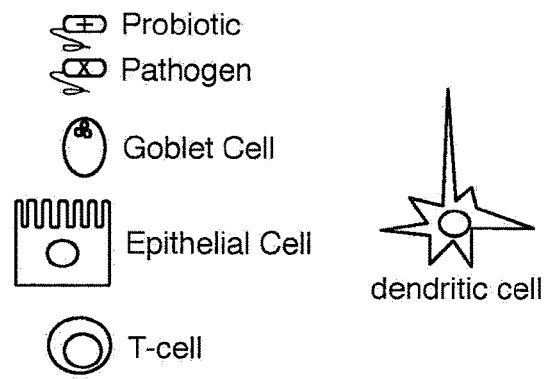
FIG. 11

MICROORGANISM-RELATED SIGNIFICANCE INDEX METRICS

CROSS-REFERENCE TO RELATED APPLICATIONS

This application is the U.S. National Phase under 35 U.S.C. § 371 of International Application No. PCT/US18/51222 filed on Sep. 14, 2018, which claims the benefit of U.S. Provisional Application No. 62/558,489 filed on Sep. 14, 2017, which are each incorporated in their entirety herein by reference.

TECHNICAL FIELD

The disclosure generally relates to genomics and microbiology.

BACKGROUND

A microbiome can include an ecological community of commensal, symbiotic, and pathogenic microorganisms that are associated with an organism. Characterization of the human microbiome is a complex process. The human microbiome includes over 10 times more microbial cells than human cells, but characterization of the human microbiome is still in nascent stages such as due to limitations in sample processing techniques, genetic analysis techniques, and resources for processing large amounts of data. Present knowledge has clearly established the role of microbiome associations with multiple health conditions, and has become an increasingly appreciated mediator of host genetic and environmental factors on human disease development. The microbiome is suspected to play at least a partial role in a number of health/disease-related states. Further, the microbiome may mediate effects of environmental factors on human, plant, and/or animal health. Given the profound implications of the microbiome in affecting a user's health, efforts related to the characterization of the microbiome should be pursued. However, conventional approaches for analyzing microbiomes, such as in relation to one or more microbiome-related conditions have left many questions unanswered.

BRIEF DESCRIPTION OF THE FIGURES

FIG. 8A-8D include specific examples of notifications including significance index metrics;

FIG. 10 includes variations of determining significance index metrics with one or more models;

FIG. 11 includes facilitating therapeutic intervention in a variation of an embodiment of a method;

DESCRIPTION OF THE EMBODIMENTS

Figure 1:
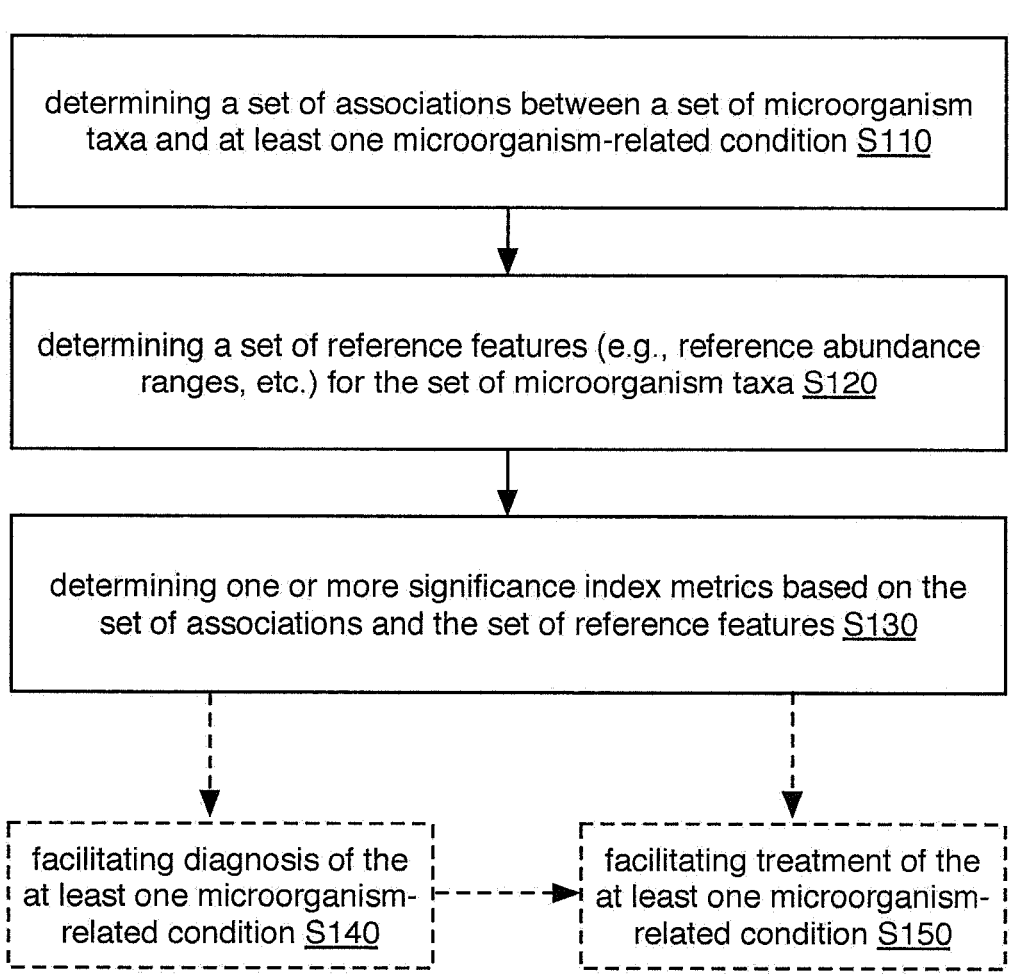
FIG. 1-2 include flowchart representations of variations of an embodiment of a method.
Figure 2:
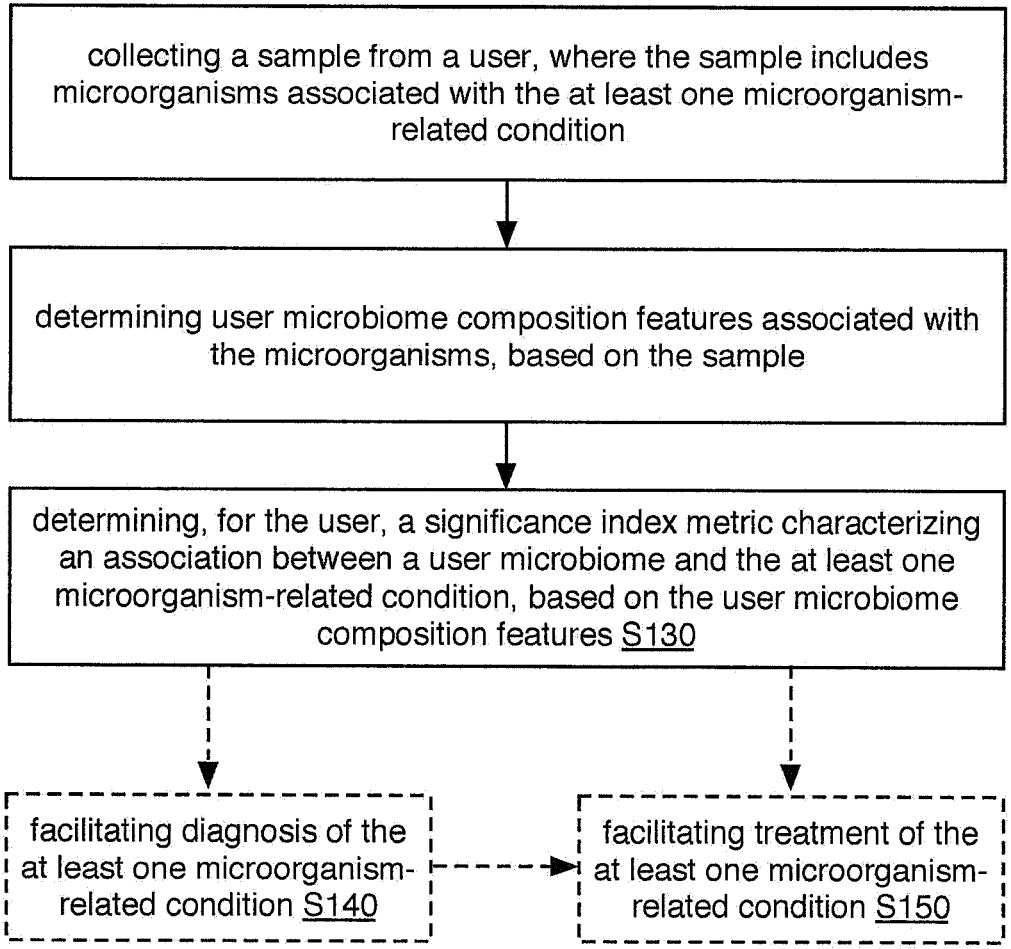

The following description of the embodiments is not intended to limit the embodiments, but rather to enable any person skilled in the art to make and use.

1. Overview

As shown in FIGS. 1-2, 4, and 9, embodiments of a method 100 (e.g., for characterizing at least one microorganism-related condition, etc.) can include: determining a set of associations (e.g., positive associations such as positive correlations, negative associations such as negative correlations, non-associations such as no correlation or minimal correlation, etc.) between a set of microorganism taxa and at least one microorganism-related condition Silo; determining a set of reference features (e.g., reference abundance ranges, etc.) for the set of microorganism taxa S120; and determining one or more significance index metrics based on the set of associations and the set of reference features S130.

In a specific example, the method 100 (e.g., for characterizing at least one microorganism-related condition, etc.) can include: determining a set of associations between a set of microorganism taxa and the at least one microorganism-related condition, where the set of associations includes at least one of positive associations, negative associations, and non-associations; associated with the at least one microorganism-related condition; determining a set of reference abundance ranges for the set of microorganism taxa, where the reference abundance ranges are associated with the at least one microorganism-related condition; and/or determining a significance index metric associated with characterization of the set of associations between the set of microorganism taxa and the at least one microorganism-related condition, based on the set of associations and the reference abundance ranges for the set of microorganism taxa.

Embodiments of the method 100 can additionally or alternatively include one or more of: facilitating diagnosis of one or more microorganism-related conditions based on the one or more significance index metrics S140; facilitating therapeutic intervention for the one or more microorganism-related conditions based on the one or more significance index metrics S150; and/or any other suitable processes.

Embodiments of the method 100 and/or system 200 can function to determine one or more metrics (e.g., significance index metrics) characterizing associations between one or more taxa and one or more microorganism-related condition (e.g., where the metrics can provide an objective measurement of the association between a combination of microorganisms and one or more microorganism-related conditions; etc.). In specific examples, significance index metrics can be used for characterizing one or more users (e.g., based on novel user samples from the users; etc.); facilitating diagnosis; facilitating therapeutic intervention; uncovering insights regarding the relationship between one or more taxa and one or more microorganism-related conditions; and/or confer any other suitable benefits.

In a specific example, the method 100 (e.g., for characterizing at least one microorganism-related condition in relation to a user, etc.) can include: collecting a sample from a user, where the sample includes microorganisms associated with the at least one microorganism-related condition; determining user microbiome composition features associated with the microorganisms, based on the sample; and/or determining, for the user, a significance index metric characterizing an association between a user microbiome and the at least one microorganism-related condition, based on the user microbiome composition features (e.g., user abundances for the set of microorganism taxa; etc.), reference microbiome composition features (e.g., reference abundances and/or abundance ranges for the set of microorganism taxa; etc.) associated with a set of microorganism taxa, and a set of associations between the set of microorganism taxa and the at least one microorganism-related condition. In variations, collecting a sample, determining microbiome features (e.g., microbiome composition features), and/or suitable processes of embodiments of the method 100 can be performed in any suitable manner described in and/or analogous to U.S. application Ser. No. 16/115,542 filed 28 Aug. 2018 and/or U.S. application Ser. No. 16/047,840 filed 27 Jul. 2018, which are herein incorporated in their entireties by this reference.

Additionally or alternatively, embodiments of the method 100 and/or system 200 can function to identify microbiome features, supplemental features (e.g., derived from supplemental data, etc.), and/or other suitable data associated with (e.g., positively correlated with, negatively correlated with, etc.) one or more microorganism-related conditions, such as for use in determining significance indexes, for use as biomarkers (e.g., for diagnostic processes, for treatment processes, etc.), for use in diagnostics and/or therapeutics, and/or for other suitable purposes. In examples, microorganism-related conditions (and/or significance indexes and/or other suitable aspects) can be associated with at least one or more of microbiome composition (e.g., microbiome composition diversity, etc.), microbiome function (e.g., microbiome functional diversity, etc.), and/or other suitable microbiome-related aspects.

Additionally or alternatively, embodiments of the method 100 and/or system 200 can function to determine one or more metrics (e.g., significance index metrics) for a panel of microorganism-related conditions (e.g., a panel categorized by condition type; etc.), such as in relation to characterizing a plurality of associations between a plurality of taxa and a plurality of microorganism-related conditions (e.g., where any number of taxa can be associated with any number of microorganism-related conditions in any suitable numerical relationship; etc.). Additionally or alternatively, embodiments can perform any suitable functionality described herein.

Figure 13:
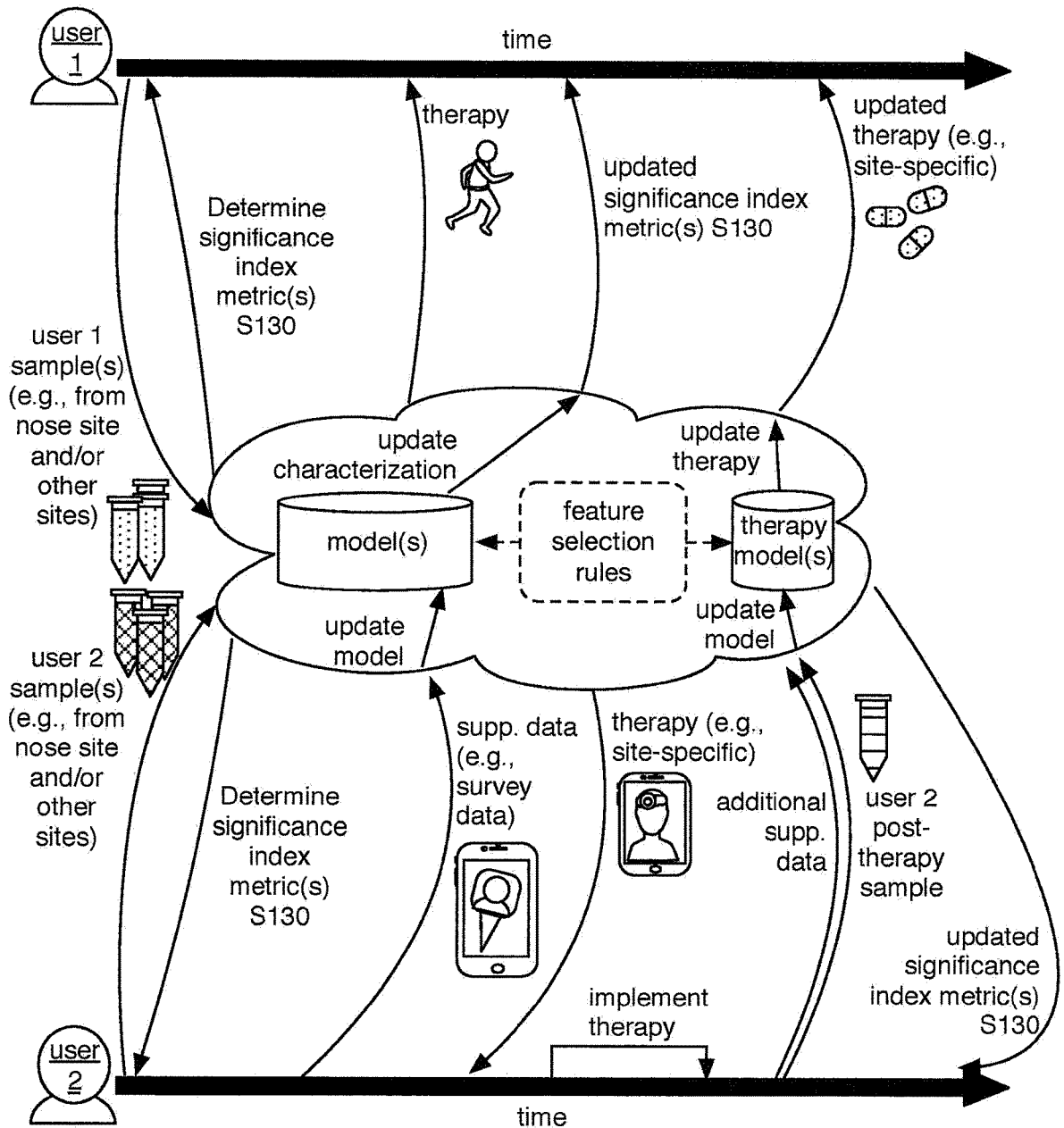
FIG. 13 includes a schematic representation of variations of an embodiment of the method.

In variations, data from populations of users (e.g., populations of subjects associated with one or more microorganism-related conditions; positively correlated, negatively correlated, not correlated, with one or more microorganism-related conditions; data derived from information sources such as scientific peer-reviewed articles; etc.) can be used to determine significance index metrics, such as for characterizing subsequent users, such as for indicating microorganism-related states of health and/or areas of improvement (e.g., for diagnostic purposes, etc.), and/or to facilitate therapeutic intervention (e.g., promoting one or more therapies; facilitating modulation of the composition and/or functional diversity of a user's microbiome toward one or more of a set of desired equilibrium states, such as states correlated with improved health states associated with one or more microorganism-related conditions; etc.), such as in relation to one or more microorganism-related conditions. Variations of the method 100 can further facilitate selection, monitoring (e.g., efficacy monitoring, etc.) and/or adjusting of therapies provided to a user, such as through collection and analysis (e.g., with significance index models) of additional samples from a user over time (e.g., throughout the course of a therapy regimen, through the extent of a user's experiences with microorganism-related conditions; as shown in. FIG. 13; etc.), across body sites (e.g., across sample collection sites of a user, such as collection sites corresponding to a particular body site type such as a nose site, gut site, mouth site, skin site, genital site; etc.), in addition or alternative to processing supplementary data over time, such as for one or more microorganism-related conditions. However, data from populations, subgroups, individuals, and/or other suitable entities can be used by any suitable portions of embodiments of the method 100 and/or system 200 for any suitable purpose.

In variations, embodiments of the method 100 and/or system 200 can determine significance index metrics for determining one or more microorganism-related characterizations and/or therapies associated with one or more microorganism-related conditions, such as characterizations and/or therapies described in U.S. application Ser. No. 16/047,840 filed 27 Jul. 2018, which is herein incorporated in its entirety by this reference.

Embodiments of the method 100 and/or system 200 can additionally or alternatively generate and/or promote (e.g., provide; present; notify regarding; etc.) characterizations (e.g., diagnoses, etc.) and/or therapies for one or more microorganism-related conditions.

Microorganism-related conditions can include one or more of: diseases, symptoms, causes (e.g., triggers, etc.), disorders, associated risk (e.g., propensity scores, etc.), associated severity, behaviors (e.g., caffeine consumption, alcohol consumption, sugar consumption, habits, diets, etc.), and/or any other suitable aspects associated with microorganism-related conditions. Microorganism-related conditions can include one or more disease-related conditions, which can include any one or more of: gastrointestinal-related conditions (e.g., irritable bowel syndrome, inflammatory bowel disease, ulcerative colitis, celiac disease, Crohn's disease, bloating, hemorrhoidal disease, constipation, reflux, bloody stool, diarrhea, etc.); allergy-related conditions (e.g., allergies and/or intolerance associated with wheat, gluten, dairy, soy, peanut, shellfish, tree nut, egg, etc.); locomotor-related conditions (e.g., gout, rheumatoid arthritis, osteoarthritis, reactive arthritis, multiple sclerosis, Parkinson's disease, etc.); cancer-related conditions (e.g., lymphoma; leukemia; blastoma; germ cell tumor; carcinoma; sarcoma; breast cancer; prostate cancer; basal cell cancer; skin cancer; colon cancer; lung cancer; cancer conditions associated with any suitable physiological region; etc.); cardiovascular-related conditions (e.g., coronary heart disease, inflammatory heart disease, valvular heart disease, obesity, stroke, etc.); anemia conditions (e.g., thalassemia; sickle cell; pernicious; fanconi; haemolyitic; aplastic; iron deficiency; etc.); neurological-related conditions (e.g., ADHD, ADD, anxiety, Asperger's syndrome, autism, chronic fatigue syndrome, depression, etc.); autoimmune-related conditions (e.g., Sprue, AIDS, Sjogren's, Lupus, etc.); endocrine-related conditions (e.g., obesity, Graves' disease, Hashimoto's thyroiditis, metabolic disease, Type I diabetes, Type II diabetes, etc.); skin-related conditions (e.g., acne, dermatomyositis, eczema, rosacea, dry skin, psoriasis, dandruff, photosensitivity, rough skin, itching, flaking, scaling, peeling, fine lines or cracks, gray skin in individuals with dark skin, redness, deep cracks such as cracks that can bleed and lead to infections, itching and scaling of the skin in the scalp, oily skin such as irritated oily skin, skin sensitivity to products such as hair care products, imbalance in scalp microbiome, etc.); Lyme disease conditions; communication-related conditions; sleep-related conditions; metabolic-related conditions; weight-related conditions; pain-related conditions; genetic-related conditions; chronic disease; and/or any other suitable type of disease-related conditions.

In variations, microorganism-related conditions can include one or more women's health-related conditions (e.g., reproductive system-related conditions; etc.) described in U.S. application Ser. No. 16/115,542 filed 28 Aug. 2018, which is herein incorporated in its entirety by this references, such as where significance index metrics can be determined and/or used for one or more women's health-related conditions and/or other suitable microorganism-related conditions.

Additionally or alternatively, microorganism-related conditions can include one or more human behavior conditions which can include any one or more of: diet-related conditions (e.g., caffeine consumption, alcohol consumption, sugar consumption, artificial sweetener consumption, omnivorous, vegetarian, vegan, sugar consumption, acid consumption other food item consumption, dietary supplement consumption, dietary behaviors, etc.), probiotic-related behaviors (e.g., consumption, avoidance, etc.), habituary behaviors (e.g., smoking; exercise conditions such as low, moderate, and/or extreme exercise conditions; etc.), menopause, other biological processes, social behavior, other behaviors, and/or any other suitable human behavior conditions. Conditions can be associated with any suitable phenotypes (e.g., phenotypes measurable for a human, animal, plant, fungi body, etc.). In variations, portions of embodiments of the method 100 and/or system 200 can be used for facilitating promoting (e.g., providing; recommending; etc.) of one or more targeted therapies to users suffering from one or more microorganism-related conditions (e.g., skin-related conditions, etc.), such as based on one or more significance index metrics.

In variations, samples (e.g., described herein) can correspond to a one or more collection sites including at least one of a gut collection site (e.g., corresponding to a body site type of a gut site), a skin collection site (e.g., corresponding to a body site type of a skin site), a nose collection site (e.g., corresponding to a body site type of a nose site), a mouth collection site (e.g., corresponding to a body site type of a mouth site), and a genitals collection site (e.g., corresponding to a body site type of a genital site).

Embodiments of the method 100 and/or system 200 can be implemented for a single user, such as in relation to applying one or more sample handling processes and/or significance index determination processes for processing one or more biological samples (e.g., collected across one or more collection sites, etc.) from the user for determining a significance index metric for the user, for microbiome-related characterization, facilitating therapeutic intervention, and/or for any other suitable purpose. Additionally or alternatively, embodiments can be implemented for a population of subjects (e.g., including the user, excluding the user), where the population of subjects can include subjects similar to and/or dissimilar to any other subjects for any suitable type of characteristics (e.g., in relation to microorganism-related conditions, demographic characteristics, behaviors, microbiome composition and/or function, etc.); implemented for a subgroup of users (e.g., sharing characteristics, such as characteristics affecting microorganism-related characterization and/or therapy determination; etc.); implemented for plants, animals, microorganisms, and/or any other suitable entities. Thus, information derived from a set of subjects (e.g., population of subjects, set of subjects, subgroup of users, etc.) can be used to provide additional insight for subsequent users. In a variation, an aggregate set of biological samples is associated with and processed for a wide variety of subjects, such as including subjects of one or more of: different demographic characteristics (e.g., genders, ages, marital statuses, ethnicities, nationalities, socio-economic statuses, sexual orientations, etc.), different microorganism-related conditions (e.g., health and disease states; different genetic dispositions; etc.), different living situations (e.g., living alone, living with pets, living with a significant other, living with children, etc.), different dietary habits (e.g., omnivorous, vegetarian, vegan, sugar consumption, acid consumption, caffeine consumption, etc.), different behavioral tendencies (e.g., levels of physical activity, drug use, alcohol use, etc.), different levels of mobility (e.g., related to distance traveled within a given time period), and/or any other suitable characteristic (e.g., characteristics influencing, correlated with, and/or otherwise associated with microbiome composition and/or function, etc.). In examples, as, the number of subjects increases, the predictive power of processes implemented in portions of embodiments of the method mo and/or system 200 can increase, such as in relation to characterizing subsequent users (e.g., with varying characteristics, etc.) based upon their microbiomes (e.g., in relation to different collection sites for samples for the users, etc.). However, portions of embodiments of the method loci and/or system 200 can be performed and/or configured in any suitable manner for any suitable entity or entities.

In variations, portions of embodiments of the method 100 can be repeatedly performed in any suitable order and/or any suitable components of embodiments of the system 200 can be repeatedly applied, such as to improve any suitable portions of embodiments of the method loco and/or any suitable components of embodiments of the system 200. In variations, the method loci can be repeatedly performed to enable refining of one or more microorganism-related databases (e.g., including associations between microorganism, taxa and microorganism-related conditions; including effect size metrics; including reference microbiome features such as reference abundance ranges; etc.), such as by collecting and analyzing additional information sources, samples (e.g, such as samples collected from subjects over time, the course of one or more microorganism-related conditions, and/or therapeutic interventions; etc.), and/or other suitable components. In variations, the method 100 can include refining processes for determining significance index metrics, such as for improving accuracy and/or other suitable aspects associated with significance index metrics.

Data described herein (e.g., significance index metrics, effect size metrics, taxa identifiers, associations, microbiome features, user features, reference features, microorganism datasets, models, microorganism-related characterizations, supplementary data, notifications, etc.) can be associated with any suitable temporal indicators (e.g., seconds, minutes, hours, days, weeks, months, years, etc.) including one or more: temporal indicators indicating when the data was collected (e.g., temporal indicators indicating when a sample was collected; sampling time; etc.), determined, transmitted, received, and/or otherwise processed; temporal indicators providing context to content described by the data (e.g., temporal indicators associated with significance index metrics, etc.); changes in temporal indicators (e.g., changes in microbiome over time; such as in response to receiving a therapy; latency between sample collection, sample analysis, provision of a microorganism-related characterization or therapy to a user, and/or other suitable portions of embodiments of the method 100; etc.); and/or any other suitable indicators related to time.

Additionally or alternatively, parameters, metrics, inputs, outputs, and/or other suitable data can be associated with value types including: scores (e.g., propensity scores; feature relevance scores; correlation scores; covariance scores; microbiome diversity scores; severity scores; etc.); individual values (e.g., individual microorganism-related condition scores, such as condition propensity scores for different conditions, for different collection sites, etc.), aggregate values, (e.g., overall scores based on individual microorganism-related scores for different conditions, collection sites, taxa; etc.), binary values (e.g., classifications of a health sample or a sample presenting a microorganism-related condition; etc.), relative values (e.g., relative taxonomic group abundance, relative microbiome function abundance, relative feature abundance, etc.), classifications (e.g., microorganism-related condition classifications and/or diagnoses for users; feature classifications; behavior classifications; demographic characteristic classifications; etc.), confidence levels (e.g., associated with significance index metrics and/or other suitable data; etc.), identifiers, values along a spectrum, and/or any other suitable types of values. Any suitable types of data described herein can be used as inputs (e.g., for different analytical techniques, models, and/or other suitable components described herein), generated as outputs (e.g., of different analytical techniques, models, etc.), and/or manipulated in any suitable manner for any suitable components associated with the method 100 and/or system 200.

One or more instances and/or portions of embodiments of the method 100 and/or processes described herein can be performed asynchronously (e.g., sequentially), concurrently (e.g., parallel data processing; concurrent cross-condition analysis; multiplex sample processing; performing sample processing and analysis for substantially concurrently evaluating a panel of microorganism-related conditions; computationally determining significance index metrics, microorganism datasets, microbiome features, and/or characterizing microorganism-related conditions in parallel for a plurality of users; such as concurrently on different threads for parallel computing to improve system processing ability; etc.), in temporal relation (e.g., substantially concurrently with, in response to, serially, prior to, subsequent to, etc.) to a trigger event (e.g., performance of a portion of the method 100), and/or in any other suitable order at any suitable time and frequency by and/or using one or more instances of the system 200, components, and/or entities described herein.

Additionally or alternatively, embodiments of the method 100 and/or system 200 can perform any suitable sample processing operations described in U.S. application Ser. No. 16/115,542 filed 28 Aug. 2018, such as for determining microorganism datasets and/or microbiome features usable in determining one or more significance index metrics. For example, embodiments of the method 100 and/or system 200 can generate microorganism sequence datasets and/or other suitable microorganism data based on applying one or more sequencing systems 215 (e.g., next-generation sequencing systems, sequencing systems for targeted amplicon sequencing, sequencing-by-synthesis techniques, capillary sequencing technique, Sanger sequencing, pyrosequencing techniques, nanopore sequencing techniques, etc.) for sequencing one or more biological samples (e.g., sequencing microorganism nucleic acids from the biological samples, etc.). Next-generation sequencing systems (e.g., next-generation sequencing platforms, etc.) can include any suitable sequencing systems (e.g., sequencing platforms, etc.) for one or more of high-throughput sequencing (e.g., facilitated through high-throughput sequencing technologies; massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, Single molecule real time (SMRT) sequencing, Nanopore DNA sequencing, etc.), any generation number of sequencing technologies (e.g., second-generation sequencing technologies, third-generation sequencing technologies, fourth-generation sequencing technologies, etc.), amplicon-associated sequencing (e.g., targeted amplicon sequencing), sequencing-by-synthesis, tunneling currents sequencing, sequencing by hybridization, mass spectrometry sequencing, microscopy-based techniques, and/or any suitable next-generation sequencing technologies.

Figure 3:
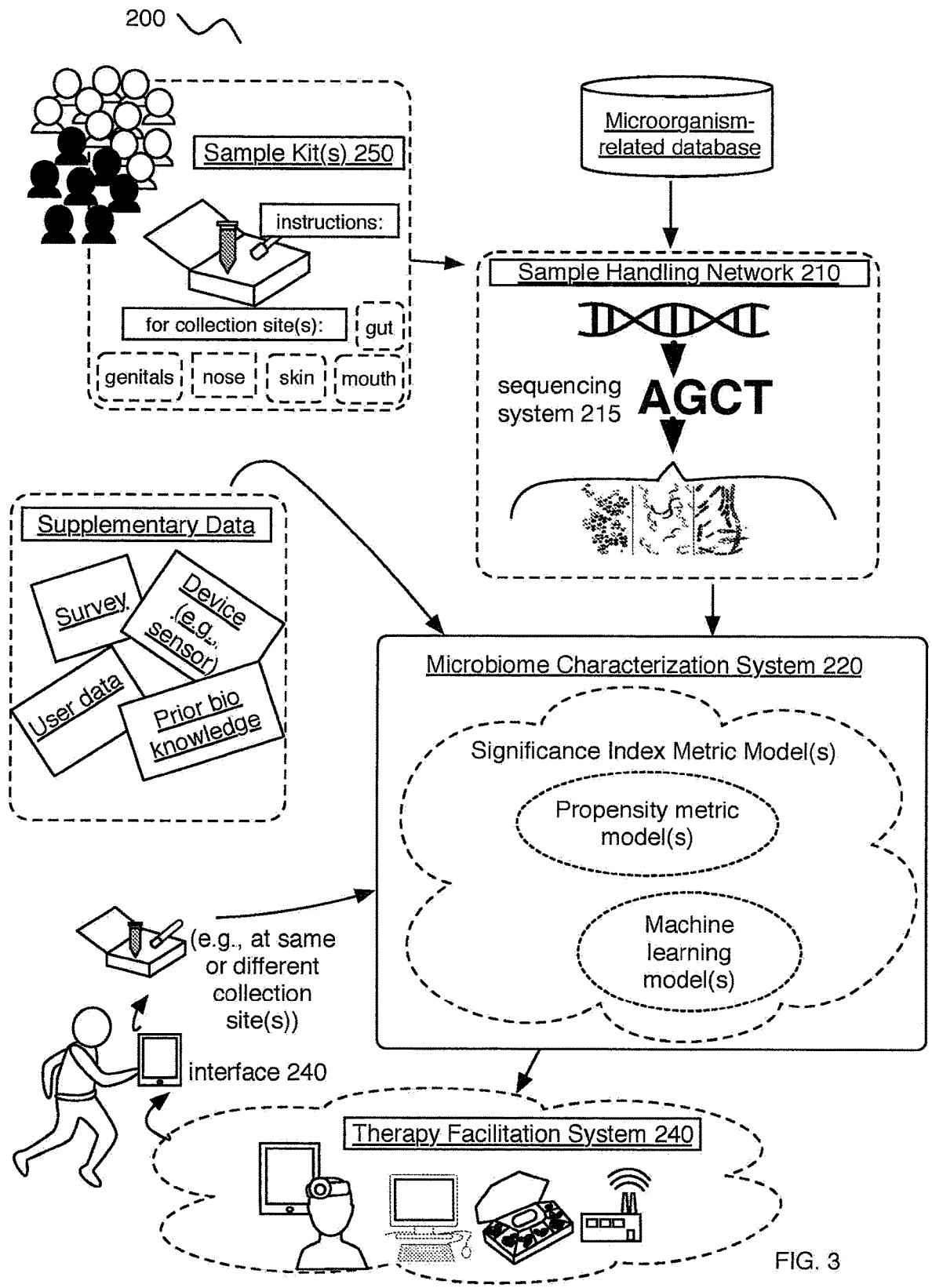
FIG. 3 includes variations of embodiments of a system.
Figure 4:
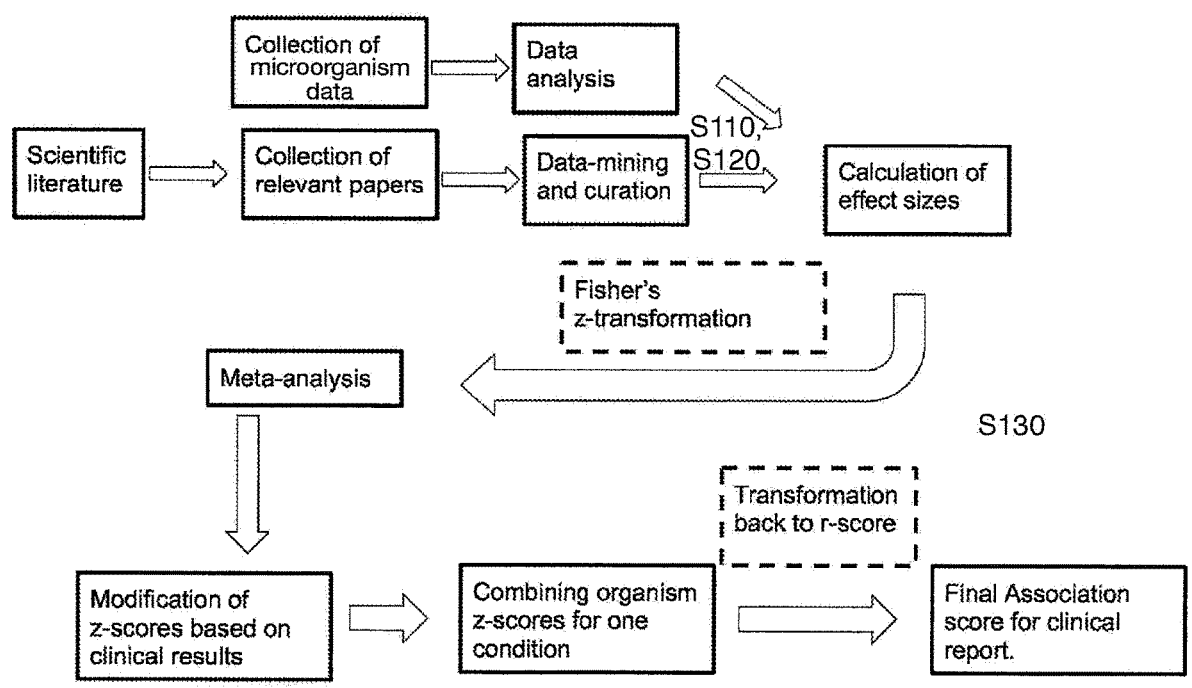
FIG. 4 includes flowchart representations of variations of an embodiment of a method.

As shown in FIG. 3, embodiments of the system 200 (e.g., for characterizing a microorganism-related condition) can include any one or more of: a handling system (e.g., a sample handling system; including a sequencing system 215; etc.) 210 operable to collect and/or process biological samples (e.g., collected by users and included in containers including pre-processing reagents; etc.) from one or more users (e.g., a human subject, patient, animal subject, environmental ecosystem, care provider, etc.) for facilitating determination of a microorganism dataset (e.g., microorganism genetic sequences; microorganism sequence dataset; etc.); a microorganism-related characterization system 220 operable to determine significance index metrics, features (e.g., microbiome composition features; microbiome functional features; diversity features; relative abundance ranges; such as based on a microorganism dataset and/or other suitable data; etc.), and/or microorganism-related characterizations (e.g., microorganism-related condition characterizations, therapy-related characterizations, characterizations for users, etc.); a therapy faciliation system 230 operable to facilitate therapeutic intervention (e.g., promote a therapy, etc.) for one or more microorganism-related conditions (e.g., based on one or more significance index metrics; for improving one or more microorganism-related conditions; etc.); an interface 240 for presenting significance index metrics and/or other suitable data; sample kits 250 for collecting one or more samples; and/or other suitable components. While the components of embodiments of the system 200 are generally described as distinct components, they can be physically and/or logically integrated in any manner. In an example, embodiments of the system 200 can omit a therapy facilitation system 230. Additionally or alternatively, the functionality of embodiments of the system 200 can be distributed in any suitable manner amongst any suitable system components. However, the components of embodiments of the system 200 can be configured in any suitable manner.

However, the method 100 and/or system 200 can be configured in any suitable manner.

2.1 Determining a Set of Associations.

Embodiments of the method 100 can include determining a set of associations between one or more microorganism taxa and one or more microorganism-related conditions S110, which can function to determine associations for use in determination of significance index metrics.

Associations can include any one or more of positive associations (e.g. positive correlations; causative associations; etc.); negative associations (e.g., negative correlations; causative associations; etc.); non-associations (e.g., no correlation; etc.); and/or any other types of associations (e.g., relationships, connections between, etc.) between one or more taxa and one or more microorganism-related conditions.

Any suitable number of taxa can be associated with any suitable number of microorganism-related conditions, in any suitable numerical relationship (e.g., 1 to many; many to 1, etc.).

Determining a set of associations can include processing condition-related information sources (e.g., third-party information sources such as scientific literature, clinical tests, etc.; sources including information regarding conditions, associated microorganism taxa, associated markers; proprietary sources; first-party sources; etc.). In a variation, Block S110 can include manually processing condition-related information sources (e.g., with human curation of markers, associations, effect sizes, data usable for calculating effect sizes, and/or associated information, etc.) to determine the set of associations and/or other suitable parameters. In another variation, Block S110 can include automatically processing condition-related information sources. For example, Block S110 can include: generating a list of online information sources; obtaining the online information sources based on the list; processing the online information sources to extract a set of taxa, associated conditions, and/or other associated data (e.g., through applying natural language processing techniques, etc.) for generating the set of associations and/or other suitable data. In another example, automatically processing information sources can include applying natural language processing approaches and/or other suitable approaches for analysis of the information sources, such as for extracting types of taxa associated with one or more microorganism-related conditions.

In variations, determining a set of associations can be based on one or more conditions (e.g., using the association, such as for downstream processing in determining one or more significance index metrics, if the conditions are met; updating a microorganism-related database with the association; etc.). Conditions can include any one or more of: subject conditions such as in relation to subject type such as human or animal, characteristics regarding the human or animal, etc.; sample conditions such as in relation to the sampling site for the samples used in identification of the one or more associations; analytical technique conditions such as in relation to types of analytical techniques used in identification of the associations; metric conditions such as in relation to the types of metrics provided by information sources and/or used in characterizing the associations; and/or any other suitable types of conditions.

In a specific example, determining associations can be based on two conditions (e.g., using the association, such as for downstream processing in determining one or more significance index metrics, if the two conditions are met; updating a microorganism-related database with the association if the two conditions are met; etc.) including: (1) samples used in the information sources were from adult humans and collected from an appropriate sampling site; and (2) appropriate metrics (e.g., statistics) are available (e.g., provided by the information source; etc.), such as including metrics accounting for the direction of the association (e.g., whether a positive association between a taxon and a microorganism-related condition, a negative association between a taxon and a microorganism-related condition, or a non-association between a taxon and a microorganism-related condition; etc.), effect size metrics (e.g., coefficients of correlation, such as between abundances of one or more microorganism taxa and one or more microorganism-related conditions; z-scores, etc.) and/or data enabling calculation of effect size metrics (e.g., where such metrics can be transformed into effect size metrics such as coefficients of correlation and/or z-scores, etc.), such as one or more of mean, standard deviation, sample sizes, odds ratios, risk ratios, proportions of individuals in the control and study groups with and without the condition and/or any other suitable metrics. In a specific example, determining one or more associations can be based on (e.g., using the association, such as for downstream processing in determining one or more significance index metrics, if the condition is met; updating a microorganism-related database with the association; etc.) the probability of regarding a false or spurious effect as true is less than 5% (i.e. P-Value<0.05), such as indicating there is a statistically significant association between the taxon and a microorganism-related condition. In a specific example, determining associations can be based on (e.g., using the association, such as for downstream processing in determining one or more significance index metrics, if the condition is met; updating a microorganism-related database with the association; etc.) the significance of the statistical comparison between the study and the control groups, such as based on the P-value, where a P-Value of less than 5% indicates the association is statistically significant. However, conditions for determining associations can be configured in any suitable manner.

In variations, determining one or more associations can include determining one or more parameters describing the one or more associations. Parameters describing the one or more associations can include any one or more of: effect size metrics (e.g., coefficients of correlation, such as between abundances of one or more microorganism taxa and one or more microorganism-related conditions; z-scores, etc.), data enabling calculation of effect size metrics, mean, standard deviation, sample sizes, odds ratios, risk ratios, proportions of individuals in the control and study groups with and without the condition and/or any other suitable metrics, experimental parameters, confidence levels, sample characteristics, parameters associated with types of conditions (e.g., subject parameters; sample parameters; analytical technique parameters; metric parameters; etc.), parameters provided by information sources, and/or any other suitable types of parameters.

Determining a set of associations (and/or microbiome features, reference features, user features, etc.) can be based on microorganism datasets (e.g., microbiome features; associated with one or more microorganism-related conditions; etc.), supplementary datasets, and/or other suitable data, such as in a manner including and/or analogous to that described in U.S. application Ser. No. 16/115,542 filed 28 Aug. 2018 and/or U.S. application Ser. No. 16/047,840 filed 27 Jul. 2018, which are herein incorporated in their entireties by this reference.

Determining a set of associations can include generating and/or updating (e.g., refining, adding to, deleting data, etc.) one or more microorganism-related databases based on the determined set of associations (e.g., adding additional associations to the one or more microorganism-related databases), such as in response to determining the set of associations, but generating and/or updating microorganism-related databases can be performed in any suitable manner at any suitable time and frequency.

However, determining a set of associations (e.g., between one or more taxa and one or more microorganism-related conditions; etc.) and/or any suitable parameters (e.g., effect size estimates, other data, etc.) Silo can be performed in any suitable manner.

2.2 Determining a Set of Reference Features.

Embodiments of the method 100 can include determining a set of reference features (e.g., reference abundance ranges, etc.) for one or more microorganism taxa (e.g., microorganism taxa for which associations were determined with one or more microorganism-related conditions; etc.) S120, which can function to determine features for use in determination of significance index metrics.

Reference features are preferably associated with (e.g., describe, correspond to, etc.) one or more microorganism taxa, such as one or more microorganism taxa for which associations with one or more microorganism-related conditions are determined (e.g., in relation to S110). Additionally or alternatively, reference features can be associated with any one or more of microbiome composition (e.g., microbiome composition diversity, etc.), microbiome function (e.g., microbiome functional diversity, etc.), any suitable subjects and/or users (e.g., any suitable groups, subgroups, and/or sets of subjects and/or users), and/or any other suitable aspects.

Reference features preferably include reference abundance ranges (e.g., reference relative abundance ranges) for one or more taxa associated with one or more microorganism-related conditions. In examples, reference abundance ranges (and/or user abundance ranges corresponding to one or more users, and/or any suitable abundance ranges; etc.) can include one or more healthy abundance ranges (e.g., corresponding to a healthy range of abundance of a taxon associated with a microorganism-related condition, such as a health range derived based on subjects without the microorganism-related condition; etc.), unhealthy abundance ranges (e.g., corresponding to a unhealthy range of abundance of a taxon associated with a microorganism-related condition, such as an unhealthy range derived based on subjects with the microorganism-related condition; etc.), low abundance ranges, normal abundance ranges, high abundance ranges, absent abundance, medium abundance ranges, percentiles for ranges (e.g., in relation to any suitable group of subjects, samples, etc.), and/or any other suitable types of abundance ranges. However, microorganism abundance ranges can be configured in any suitable manner.

Reference features can be determined from the same or different information sources used in variations of determining associations between one or more taxa and one or more microorganism-related conditions (e.g., a same information source providing reference features such as reference abundance ranges for associations between a set of taxa and a microorganism-related condition.

Additionally or alternatively, reference features can be determined in any suitable manner analogous to or different to determining one or more associations between taxa and microorganism-related conditions. In variations, determining reference features can include determining reference features based on sample processing and bioinformatics analysis for collected samples from an aggregate population of subjects associated with one or more microorganism-related conditions (e.g., including a subgroup of subjects with the condition; a control subgroup of subjects without the condition; etc.). In variations, determining reference features can be based on one or more of information sources, empirical analysis, sample processing, bioinformatics analysis, and/or any other suitable processes.

Determining reference features, user features, and/or any suitable portions of embodiments of the method 100 can include applying pre-preprocessing (e.g., for data extracted from information sources, for microorganism datasets, microbiome features, and/or other suitable data for facilitation of downstream processing such as determining significance index metrics, etc.). In an example, performing a characterization process can include, filtering a dataset (e.g., filtering a dataset extracted from an information source, filtering a microorganism sequence dataset, such as prior to applying a set of analytical techniques to determine the microbiome features such as reference features, etc.), by at least one of: removing first sample data corresponding to first sample outliers of a set of biological samples (e.g., associated with one or more microorganism-related conditions, etc.), such as where the first sample outliers are determined by at least one of principal component analysis, a dimensionality reduction technique, and a multivariate methodology; removing second sample data corresponding to second sample outliers of the set of biological samples, where the second sample outliers can determined based on corresponding data quality for the set of microbiome features (e.g., removing samples corresponding to a number of microbiome features with high quality data below a threshold condition, etc.); c) removing one or more microbiome features from the set of microbiome features based on a sample number for the microbiome feature failing to satisfy a threshold sample number condition, where the sample number corresponds to a number of samples associated with high quality data for the microbiome feature; and/or any other suitable filtering techniques for any suitable data described herein. However, pre-processing can be performed with any suitable analytical techniques in any suitable manner.

Determining reference features, user features, and/or other suitable features (e.g., microbiome features, supplementary features, etc.) can use computational methods (e.g., statistical methods, machine learning methods, artificial intelligence methods, bioinformatics methods, other approaches described herein, etc.) to characterize a subject, sample, dataset, and/or other suitable component as exhibiting and/or otherwise associated with one or more features (e.g., where determining user microbiome features can include determining feature values for microbiome features identified as correlated with and/or otherwise associated with one or more microorganism-related conditions, etc.), such as features characteristic of a set of users with the one or more microorganism-related conditions, etc.). However, any suitable analytical techniques (e.g., described herein) can be used in determining features and/or performing suitable portions of embodiments of the method 100. In an example, determining reference features and/or suitable features can include applying a set of analytical techniques including at least one of a univariate statistical test, a multivariate statistical test, a dimensionality reduction technique, and an artificial intelligence approach, such as where the features can improve computing system-related functionality associated with the determining of significance index metrics (e.g., in relation to accuracy, reducing error, processing speed, scaling, etc.). In an example, determining microbiome features (e.g., user microbiome features, etc.) can include applying a set of analytical techniques to determine at least one of presence of at least one of a microbiome composition diversity feature and a microbiome functional diversity feature, absence of the at least one of the microbiome composition diversity feature and the microbiome functional diversity feature, a relative abundance feature describing relative abundance of different taxonomic groups associated with the first microorganism-related condition, a ratio feature describing a ratio between at least two microbiome features associated with the different taxonomic groups, an interaction feature describing an interaction between the different taxonomic groups, and a phylogenetic distance feature describing phylogenetic distance between the different taxonomic groups, such as in relation to (e.g., associated with) one or more microorganism-related conditions, and such as where the set of analytical techniques can include at least one of a univariate statistical test, a multivariate statistical test, a dimensionality reduction technique, and an artificial intelligence approach.

In variations, upon identification of represented groups of microorganisms of the microbiome associated with one or more samples (e.g., from subjects with or without one or more microorganism-related conditions; etc.), features associated with (e.g., derived from) compositional and/or functional aspects of the microbiome can be determined. In a variation, generating features can include generating features based upon multilocus sequence typing (MSLT), in order to identify markers useful for significance index metric determination and/or suitable portions of embodiments of the method 100. Additionally or alternatively, determining features can include determining features that describe the presence or absence of certain taxonomic groups of microorganisms, and/or ratios between exhibited taxonomic groups of microorganisms. Additionally or alternatively, determining features can include determining features describing one or more of: quantities of represented taxonomic groups (e.g., taxa), networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional aspect(s).

Additionally or alternatively, determining features can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, determining features can include generating statistical measures of taxonomic variation, as derived from abundance metrics. Additionally or alternatively, determining features can include determining features associated with (e.g., derived from) relative abundance factors (e.g., in relation to changes in abundance of a taxon, which affects abundance of other taxa). Additionally or alternatively, determining features can include generation of qualitative features describing presence of one or more taxonomic groups, in isolation and/or in combination. Additionally or alternatively, determining features can include generation of features related to genetic markers (e.g., representative 16S, 18S, and/or ITS sequences) characterizing microorganisms of the microbiome associated with a biological sample. Additionally or alternatively, determining features can include generation of features related to functional associations of specific genes and/or organisms having the specific genes. Additionally or alternatively, determining features can include generation of features related to pathogenicity of a taxon and/or products attributed to a taxon. Additionally or alternatively, determining features can include determination of any other suitable feature(s), such as derived from information sources, sequencing and mapping of nucleic acids of a biological sample, and/or any suitable approaches. For instance, the feature(s) can be combinatory (e.g. involving pairs, triplets), correlative (e.g., related to correlations between different features), and/or related to changes in features (e.g., temporal changes, changes across sample sites, etc., spatial changes, etc.).

In variations, determining features can include determining one or more site-specific associated with one or more collection sites (e.g., gut site, nose site, skin site, genital site, mouth site, etc.). In an example, a set of site-specific features can include a first subset of site-specific features associated with a first body site, and a second subset of site-specific features associated with a second body site. However, multi-site analyses can be performed in any suitable manner.

In variations, determining features can include applying computer-implemented rules (e.g., models, feature selection rules, etc.) to process population-level data and/or other suitable data, but can additionally or alternatively include applying computer-implemented rules to process microbiome-related data on a demographic characteristic-specific basis (e.g., subgroups sharing one or more demographic characteristics such as therapy regimens, dietary regimens, physical activity regimens, ethnicity, age, gender, weight, behaviors, etc.), condition-specific basis (e.g., subgroups exhibiting a specific microorganism-related condition, a combination of microorganism-related conditions, triggers for the microorganism-related conditions, associated symptoms, etc.), a sample type-specific basis (e.g., applying, different computer-implemented rules to process microbiome data derived from different collection sites; etc.), a user basis (e.g., different computer-implemented rules for different users; etc.) and/or any other suitable basis. In examples, determining features can include assigning users from the population of users to one or more subgroups; and applying different computer-implemented rules for determining features (e.g., the set of feature types used; the types of characterization models generated from the features; etc.) for the different subgroups. However, applying computer-implemented rules can be performed in any suitable manner for any suitable portions of embodiments of the method 100, such as for determining significance index metrics S130.

Determining features can include process can include determining one or more abundance ranges (e.g., reference microbiome parameter ranges; a healthy reference relative abundance range, where the range can be associated with a healthy microbiome and/or the absence of one or more conditions; a risk reference relative abundance range associated with the presence of and/or risk of one or more conditions; microorganism composition range for abundance of one or more taxa; phylogenetic diversity of the microorganisms present in the sample; microorganism functional diversity range for functional features associated with one or more taxa; etc.), such as reference abundance range and/or user abundance ranges, and/or any suitable abundance ranges, such as where one or more significance index metrics can be based on a comparison between the user microbiome parameter (e.g., user abundance, etc.) and the reference microbiome parameter range (e.g., characterizing a user as possessing an poor significance index metric for microbiome composition in relation to bacterial targets associated with microorganism-related conditions based on the user microbiome parameter indicating an abundance outside of the healthy reference ranges for the different bacterial targets; etc.). Microbiome parameter ranges can have any suitable lower- and upper-limits, in any suitable form (e.g., counts, etc.). Reference microbiome parameter ranges can include ranges representing any suitable confidence intervals (e.g., 99% confidence intervals across a population of users). In an example, reference relative abundance ranges can be calculated for any suitable taxa, such as based on dividing the count of reads corresponding to that taxa by the total number of reads (e.g., total number of clustered and filtered reads); however, reference relative abundance ranges can be calculated in any suitable manner.

In a variation, determining reference abundance ranges and/or suitable features can be performed empirically. For example, Block S130 can include collecting biological samples and supplementary datasets from a population of users. The population of users can include users associated with any suitable state of microbiome composition, microbiome phylogenetic diversity, microbiome functional diversity, conditions, and/or other suitable characteristics, where the supplementary datasets (e.g., digitally administered surveys at an application executing on mobile devices associated with the users) can be informative of the characteristics. In a specific example, the method 100 can include: processing biological samples from a population of healthy users; processing the biological sample to determine microorganism sequences; determining relative abundance of each taxa (e.g., from a set of taxa determined to be associated and/or potentially associated with one or more microorganism-related conditions, etc.) for each user; and generating healthy ranges (and/or unhealthy ranges) for each of the taxa based on the relative abundances across the population of healthy users. However, empirically determining reference microbiome parameter ranges can be performed in any suitable manner. In a specific example, the supplementary data can indicate a lack of the at least one microorganism related condition for a subset of subjects from a set of subjects; where determining the set of microbiome features can include determining healthy reference microbiome parameters ranges associated with the subset of subjects, based on the microorganism sequence dataset; and where determining one or more significance index, metrics can be based on the on the supplementary data and/or the healthy reference microbiome parameters ranges. In a variation, determining reference microbiome parameter ranges can be performed non-empirically, such as based on manually and/or automatically processing condition-related information sources.

Comparing one or more reference features (e.g., abundance ranges, etc.) to one or more user microbiome features (e.g., abundances, etc.) associated with one or more characteristics (e.g., taxa, conditions, etc.) can be used in determining one or more significance index metrics, such as including characterizing the user as possessing the characteristic (e.g., a healthy microbiome, etc.) or not possessing the characteristic based on whether the user microbiome parameter values fall inside or outside the reference microbiome parameter ranges.

Determining reference features can additionally or alternatively include updating reference features (e.g., at one or more microorganism-related databases; etc.), such as for improving the set of reference features used in determining one or more significance index metrics (e.g., for improving accuracy of significance index metrics, such as in relation to characterizing one or more associations between microorganism taxa and microorganism-related conditions; etc.).

However, determining reference features S120 can be performed in any suitable manner.

2.3 Determining a Significance Index Metric.

Embodiments of the method 100 can include determining one or more significance index metrics (e.g., based on the set of associations and the set of reference features, etc.) S130, which can function to determine one or more metrics associated with characterization of one or more associations between one or more microorganism taxa and one or more microorganism-related conditions.

Significance index metrics preferably describe a degree of association between a set of taxa and one or more microorganism-related conditions, but can additionally or alternatively describe users, propensity for one or more microorganism-related conditions, risk for one or more microorganism-related conditions, characteristics useable for determining one or more microorganism-related condition characterizations (e.g., diagnoses, other suitable data for facilitating diagnoses, etc.), characteristics usable for determining one or more therapies (e.g., for facilitating therapeutic intervention for one or more microorganism-related conditions; etc.), and/or can be associated with any suitable aspects.

Significance index metrics can include nay one or more of scores (e.g., expressed as a range from 0 to 100 and/or any suitable range), propensity scores for users (e.g., describing a user propensity for one or more microorganism-related conditions based on user microbiome features and/or other suitable user data; etc.), classifications (e.g., by a machine learning model; classifications of presence or absence of one or more microorganism-related conditions; any suitable classifications associated with one or more microorganism-related conditions, such as in relation to condition severity; etc.), and/or can include any suitable form of data described herein.

Significance index metrics can be for any number of associations (e.g., between taxa and microorganism-related conditions, etc.), users (e.g., propensity scores describing a user's propensity for one or more microorganism-related conditions; etc.), taxa, microorganism-related conditions, and/or any suitable components.

Determining significance index metrics and/or any suitable portions of embodiments of the method 100 and/or system 200 can include employing one or more analytical techniques including any one or more of: univariate statistical tests, multivariate statistical tests, dimensionality reduction techniques, artificial intelligence approaches (e.g., machine learning approaches, etc.), performing pattern recognition on data (e.g., identifying correlations between microorganism-related conditions and microbiome features; etc.), fusing data from multiple sources (e.g., generating characterization models based on microbiome data and/or supplementary data from a plurality of users associated with one or more microorganism-related conditions, such as based on microbiome features extracted from the data; etc.), combination of values (e.g, averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating (e.g., of characterization models and/or therapy models based on processed biological samples over time; etc.), ranking (e.g., microbiome features; therapies;

etc.), weighting (e.g., microbiome features; etc.), validating, filtering (e.g., for baseline correction, data cropping, etc.), noise reduction, smoothing, filling (e.g., gap filling), aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing techniques, other signal processing operations, other image processing operations, visualizing, and/or any other suitable processing operations.

Artificial intelligence approaches can include any one or more of: supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.) reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, $C_{4\text{-}5}$, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), an ensemble method (e.g., boosting, boostrapped aggregation, AdaBoost, stacked generalization, gradient boosting machine method, random forest method, etc.), and/or any suitable artificial intelligence approach. However, data processing can be employed in any suitable manner.

Significance index metrics can additionally or alternatively include site-specific significance index metrics (e.g., specific to one or more body sites, including any one or more of gut sites, genital sites, nose sites, skin sites, mouth sites, and/or other suitable sites; etc.), such as significance index metrics characterizing associations between one or more microorganism-related conditions and one or more taxa, where the associations are specific to a specific body site. In an example, for the same body site and microorganism-related conditions, associations with taxa can differ (e.g., can be associations with different taxa) based on one or more body sites involved (e.g., different associations for a gut site compared to a nose site; etc.). In a specific example, significance index metrics can differ (e.g., values of significance index metrics, types of significance index metrics) based on the one or more body sites involved. In examples, different site-specific significance index models can be generated, applied, and/or otherwise processed. In specific examples, different site-specific significance index models can be generated, applied, and/or otherwise processed based on different microbiome features, such as site-specific features associated with the one or more body sites that the site-specific significance index model is associated with (e.g., using gut site-specific features derived from samples collected at gut collection sites of subjects, and/or correlated with one or more microorganism-related conditions, such as for determining gut site-specific features, generating a gut site-specific significance index model that can be applied for determining significance index metrics based on user samples collected at user gut sites, and/or for any suitable purpose; etc.). Site-specific models, site-specific features, samples, site-specific therapies, and/or other suitable entities (e.g., able to be associated with a body site, etc.) are preferably associated with at least one body site (e.g., corresponding to a sample collection site; etc.) including one or more of a nose site, gut site (e.g., characterizable based on stool samples, etc.), skin site, genital site (e.g., vaginal site, etc.), mouth site, and/or any suitable body region. However, site-specific significance index metrics can be configured in any manner and determined in any suitable manner.

In a variation, determining one or more significance index metrics can be based one or more effect size metrics associated with (e.g., describing, characterizing, etc.) one or more associations between one or more taxa and one or more microorganism-related conditions. Effect size metrics preferably include coefficients of correlation (e.g., between abundance for a taxon and a microorganism-related condition) but can additionally or alternatively include z-scores, and/or any suitable types of metrics (e.g., described herein, etc.). In a specific example, determining the significance index metric can include determining effect size metrics for the set of associations between the set of microorganism taxa and the at least one microorganism-related condition, based on the set of reference abundance ranges (and/or suitable reference features) for the set of microorganism taxa; and determining the significance index metric based on the effect size metrics.

In examples, data extracted from one or more information sources (e.g., mean, standard deviation, sample sizes, proportions of individuals in the control and study groups with and without the condition, etc.) can be transformed into one or more types of effect size metrics (e.g., coefficients of correlation, etc.). In specific examples, transformations into types of effect size metrics, and/or suitable portions of determining significance metrics based on effect size metrics can be performed with one or more computing systems (e.g., remote computing systems, such as including microorganism-related databases, etc.), and/or through any suitable components. In an example, a significance index can be calculated based on an overall coefficient of correlation obtained from combination of a plurality of individual effect size metrics.

In specific examples, coefficients of correlation (e.g., obtained through transformations of data extracted from information sources such as scientific peer-reviewed articles, etc.) can be transformed to z-scores (e.g., using Fisher's transformation), such as by using $$z=0.5*[(\ln(1+r))/(\ln(1-r))]$$

where r corresponds to coefficient of correlation; where a meta-analysis can be performed (e.g., where the z-score is regarded as a dependent variable and taxa are included as independent factors; where different taxa will have different associations with (e.g., different effects on; etc.) the one or more microorganism-related conditions; such as where, an assumption can be established that the information sources used are a subset of all information sources, and the true effect size is not supposed to be the same in all cases, motivating a random effect model to be fitted and where the information sources used are included as a random effect; and where the output of the analysis can include the predicted values of z-score for each taxon; and/or where the z-scores can be transformed (e.g., transformed back) to coefficients of correlation.

Figure 5:
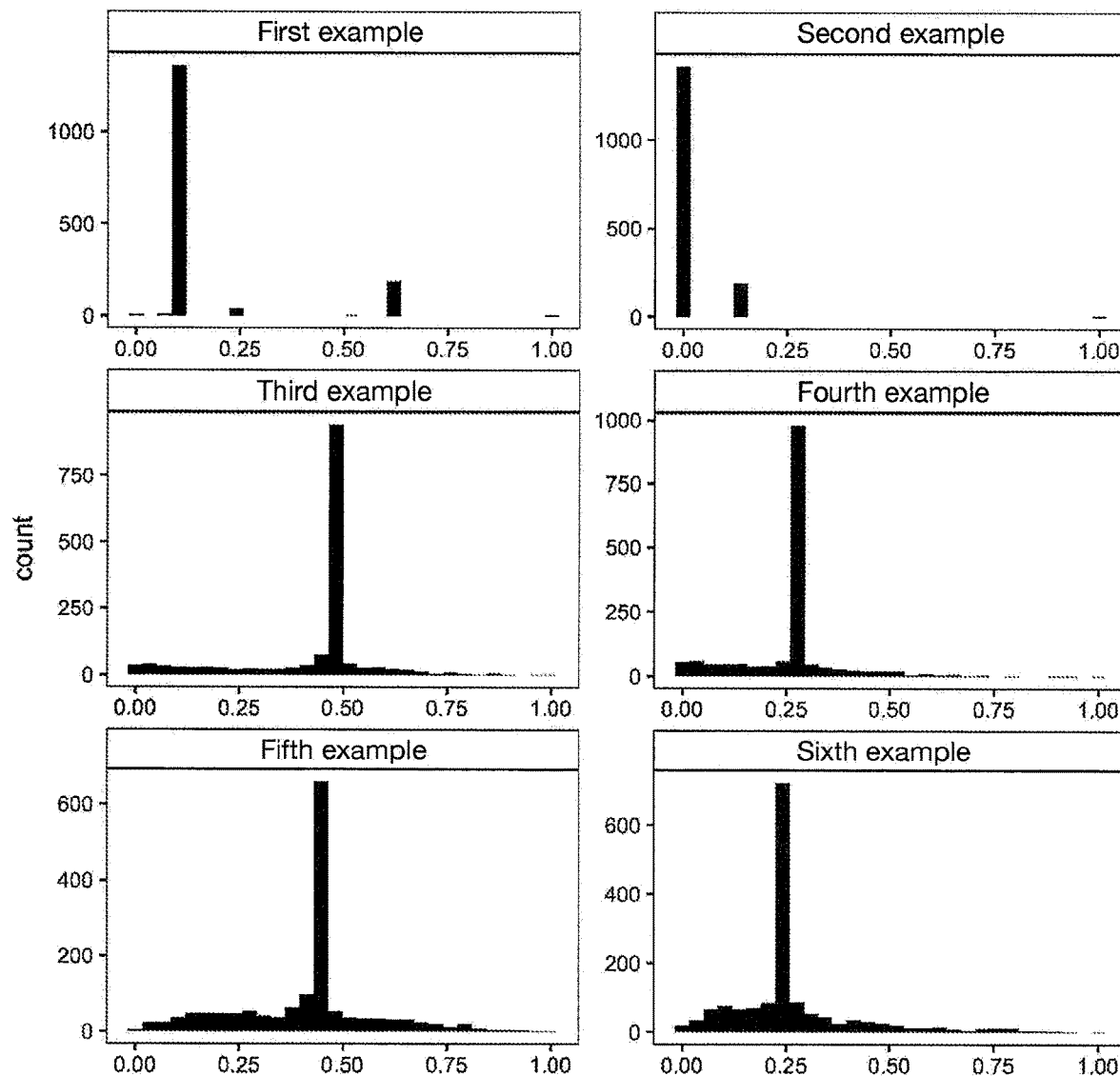
FIG. 5 includes graph representations of significance index metric frequencies in variations of an embodiment of a method.

In an example (e.g., in a first example, as shown in Table 1, such as where Table 1 includes observed and theoretical maximum and minimum values for each of the significance index metrics, which are resealed between 0 and 100; in a first example, as shown in FIG. 5, such as where FIG. 5 includes histograms of frequencies of significance index metrics for processed samples processed, such as using analytical techniques described herein, where X-axis indicates significance index metrics scaled to the range 0-1 using the maximum and minimum observed values from reference samples; where results include a single major peak corresponding to samples having 0 relative abundance on all relevant taxa; etc.), determining a significance index can be based on $$SI=1-(\Pi(1-r_a)*\Pi(1-r_{ia}))$$

where $\Pi$=product function (e.g., the first product function runs over the directly associated taxa, while the second product function runs over the inversely associated taxa), $r_a$=coefficient of correlation of the associated taxa (e.g., positive correlation; as shown in Table 2), $r_{ia}$=coefficient of correlation of the inversely associated organisms (e.g., negative correlation; as shown in Table 2); such as where according to the abundance and the direction of the association, the correlations are classified as "protective" when associated (e.g., positively associated) taxa are found in low or normal abundances, when they are not found at all in the sample, or when inversely associated (e.g., negatively associated) taxa are found in high abundance in the sample; and/or where correlations are classified as "penalty" when associated taxa are positive in the sample, when the taxa are found in high abundance, or when inversely associated taxa are found in low or normal abundance in the sample. In a specific example, determining the effect size metrics can include determining a set of coefficient of correlations for the set of associations between the set of microorganism taxa and the at least one microorganism-related condition, based on a meta-analysis; and where determining the significance index metric based on the effect size metrics can include determining the significance index metric based on the set of coefficient of correlations. In a specific example, determining the significance index metric for the user can include determining the significance index metric based on the user microbiome composition features and a set of coefficient of correlations for the set of associations between the set of microorganism taxa and the at least one microorganism-related condition.

In an example (e.g., a second example, as shown in Table 1 and FIG. 5), each z-score (e.g., from taxa found an individual's samples) can be multiplied by a factor dependent on the direction of the association (e.g., positive or negative (inverse), between the taxon and the microorganism-related condition, etc.) and on the abundance of the organism (e.g., corresponding to the taxon, etc.) in the sample (e.g., low, normal or high); where the total z-score can be determined by multiplying the individual scores from each taxon; and/or where the modified score is subtracted from to get the probability based on:

Probability=1−(z_score*abundance multiplier)

where the abundance multiplier is determined based on the abundance of the taxon and the direction of the association, such as according to:

Inversely associated/low abundance=0

Inversely associated/normal abundance=1

Inversely associated/high abundance=1

Associated/low abundance=0

Associated/normal abundance=0

Associated/high abundance =1 where additionally or alternative multipliers (e.g., weights) can be added (e.g., if needed), such as before converting the z-scores back to coefficients of correlation; and/or where the one or more total z-scores can be transformed back to coefficients of correlation such as through the inverse Fisher transformation:

$$r=[\exp(2*z)-1]/[\exp(2*z)+1]$$

where r corresponds to coefficient of correlation, and where a score from −1 to 1 can be obtained, and where to obtain the percentage of association, the score can be multiplied by 100. In a specific example, determining the effect size metrics can include determining a set of z-scores for the set of associations between the set of microorganism taxa and the at least one microorganism-related condition; and modifying the set of z-scores based on the reference abundance ranges for the set of microorganism taxa and at least one of the positive associations and the negative associations between the set of microorganism taxa and the at least one microorganism-related condition; and where determining the significance index metric based on the effect size metrics can include determining the significance index metric based on the modified set of z-scores. In a specific example, determining the significance index metric for the user can include determining the significance index metric based on the user microbiome composition features and a set of modified z-scores determined based on the reference microbiome composition features and a set of z-scores for the set of associations between the set of microorganism taxa and the at least one microorganism-related condition.

In an example, determining a significance index metric can be based on a Lowry method (e.g., for determining concentration of proteins in a sample, etc.), such as including performing a meta-analysis and weighing the outputs with one or more abundance multipliers (e.g., described above, etc.); generating mock samples and random combinations of abundances of the set of taxa (e.g., corresponding to associations with microorganism-related conditions; etc.); determining a calibration curve based on the abundances; and using real samples (e.g., from subjects, users, etc.) in an interpolation process with the calibration curve to determine significance index. In a specific example, determining the effect size metrics can include performing an interpolation process based on the reference abundance ranges and a calibration curve derived from a random set of abundances for the set of microorganism taxa; and where determining the significance index metric based on the effect size metrics can include determining the significance index metric based on the interpolation process. In a specific example, determining the significance index metric for the user can include determining the significance index metric based on user microbiome composition features (and/or suitable user microbiome features) and an interpolation process with the reference microbiome composition features (and/or suitable reference features) and a calibration curve derived from a random set of abundances for the set of microorganism taxa. However determining one or more significance index metrics based on effect size metrics can be performed in any suitable manner.

In a variation, determining one or more significance index metrics can include determining one or more propensity scores, such as based on effect size metrics and user features (e.g., user abundances, user microbiome features such as user microbiome composition features, etc.). In a specific example, determining the significance index metric can include determining a propensity score for a user describing an association between a user microbiome and the at least one microorganism-related condition, based on the effect size metrics and user abundances for the set of microorganism taxa. In a specific example, user microbiome composition features include user abundances for the set of microorganism taxa, where the reference microbiome composition features include reference abundance ranges for the set of microorganism taxa, and where determining the significance index metric includes determining a propensity score for the user characterizing the association between the user microbiome and the at least one microorganism-related condition, based on the user abundances and effect size metrics determined based on the reference abundance ranges and the set of associations between the set of microorganism taxa and the at least one microorganism-related condition.

Figure 6:
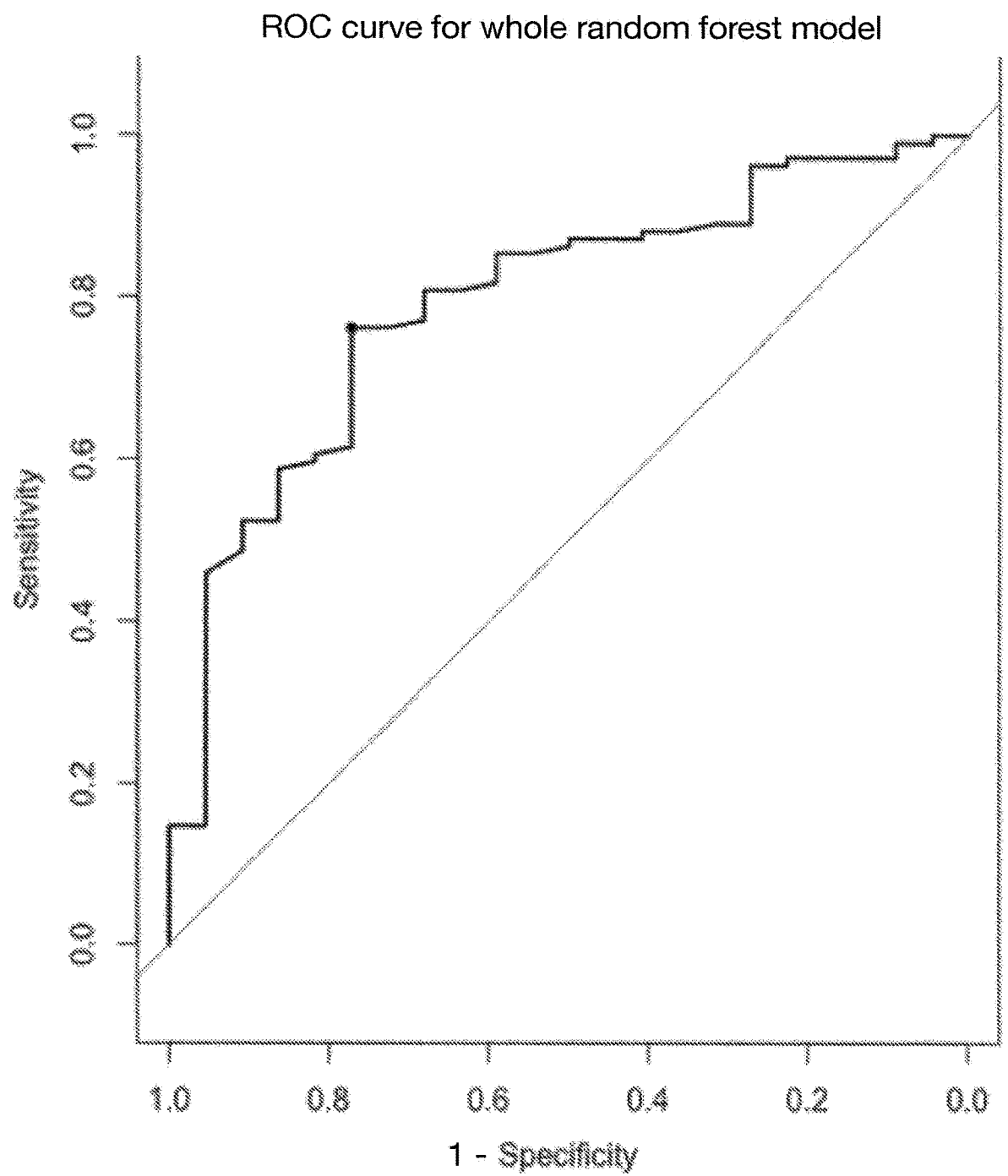
FIG. 6 includes a graph representation of metrics for a Crohn's disease prediction machine learning model in a variation of an embodiment of a method.

In an example (e.g., third example, as shown in Table 1 and FIG. 5), determining a propensity score can be based on:

$$\Sigma_{i=1}^{T} f_{th} c_T$$

where $f_{th}$ corresponds to the relative abundance of the t-th taxa on the h-th user, and where $c_t$ corresponds to the effect size. In an example (e.g., a fourth example, as shown in Table 1 and FIG. 5), determining a propensity score can be based on significance of the effect size, where determining the propensity score can be based, on:

$$\Sigma_{i=1}^{T} f_{th} p_t c_t \text{ with } p_t = BF_{10}/1 + BF_{10}$$

where the BF parameter corresponds to the Bayes Factor (e.g., as shown in Table 2), which transforms the coefficients of correlation into probabilities (e.g., as shown in Table 2). A propensity score associated with (e.g., calculated using the equation in, etc.) the third example and a propensity score associated with (e.g., calculated using the equation in, etc.) the fourth example can be formulated, respectively in a fifth and a sixth example (e.g., as shown in Table 1 and FIG. 6), by transforming the taxa frequency into a continuous range spanning from minus to positive infinity using the quantiles of a standard normal distribution (e.g., to improve apparent discontinuity on the score produced by taxa having 0 relative abundance, etc.); such as where a pseudocount of 1/10000 can be applied to the abundances for the two scores. In a specific example, determining the propensity score includes determining the propensity score based on the user abundances, the effect size metrics, and significance metrics for the effect sizes.

In examples (e.g., where variation of significance index can be affected by variation on the taxa abundance among users and magnitude of effect size metrics; etc.), propensity scores can be normalized, such as based on bounding with a predictable minimum and maximum value. In a specific example, a normalized propensity score (and/or other suitable normalized significance index metric) can be determined based on:

$$\text{normalised score} = \text{score}_h - \text{score}_{minimum}/\text{score}_{maximum} - \text{score}_{minimum}$$

such as where the minimum and maximum values can be determined empirically based on processed samples from users (e.g., where scores for the samples can cover the observed range of abundance of each taxon, etc.), determined based on information sources, and/or otherwise determined; and where the minimum and maximum values can be updatable (e.g., based on newly processed samples, etc.). In a specific example, determining the significance index metric includes normalizing the propensity score based on a set of empirical abundance ranges for the set of microorganism taxa. In a specific example, a set of vaginal samples (and/or other suitable samples) can be processed to determine empirical abundances for a set of taxa associated with human papilloma virus (HPV) (and/or other suitable microorganism-related conditions; etc.), where the minimum and maximum abundances and/or abundances corresponding to minimum and maximum significance index metric scores can be used in determining upper and lower boundaries of significance index metrics, that can be translated respectively into a score of 100 and a score of 0. In examples normalization of propensity score and/or any other suitable metrics can include one or more of: scaling the determined metrics based on observed minimum and/or maximum values of the metric type and/or parameters used in determining the metric (e.g., based on processing samples; updating based on processing new samples; etc.); filtering samples used in determining minimum and/or maximum values of the metric type, such as based on manual and/or automatic analysis (e.g., in relation to appropriateness for use, such as based on correlation with microorganism-related conditions related to the target microorganism-related condition; etc.); choosing maximum and/or minimum values as an empirical percentile of distribution of observed values from a set of samples (e.g., lower or higher $99^{th}$ percentile; etc.), such as for lowering the effect of extreme values and allowing estimation of new maximum and/or minimum value as additional data (e.g., from additional processed samples) become available; down-weighting the effect of extreme outliers without having to choose a particular percentile, such as for enabling use of all data and weighing with higher importance to a larger portion of the set of data, for reducing the effect of extreme values and enabling estimation of new maximum and minimum values automatically as more data becomes available; and/or any other suitable processes. However, determining propensity scores can be performed in any suitable manner.

In a variation, determining one or more significance index metrics can be based on one or more labels determined for (e.g., identified for, assigned to, etc.) one or more samples. In an example, labels can be assigned based on abundance of taxa, in the sample, corresponding to the set of taxa associated with the at least one microorganism-related condition. In a specific example, the method 100 can include: determining abundances for a set of taxa for a given sample; comparing the abundances to healthy abundance ranges for the each taxon associated with the one or more microorganism-related conditions; and assigning a label (e.g., a "flag") for each taxon-condition association based on Low-normal-high range of abundance: the flag applies when the taxon is directly correlated with the health condition, and abundance is 'high';

Low-normal-high range of abundance: the flag applies when the taxon is inversely correlated with the health condition, and abundance is 'low';

Absent-medium-high range of abundance: the flag applies when the taxon abundance is 'high';

Low-normal range of abundance: the flag applies when the taxon is inversely correlated with the health condition, and abundance is 'low';

Normal-high range of abundance: the flag applies when the taxon is directly correlated with the health condition, and abundance is 'high';

Negative-positive: the flag applies when the taxon is 'positive' (e.g., it has a non-zero abundance in the sample);

Where, for each microorganism-related condition, the number of assigned labels (e.g., "flags") can be counted, and the significance can be calculated based on:

$$(A/B) \times 100$$

where A=Number o f taxa with a label for a condition; and B=Total taxa associated with that condition. In a specific example, determining the significance index metric includes determining a set of labels for a user sample, where determining the set of labels includes determining a label of the set of labels for a taxon of the set of microorganism taxa based on satisfaction of an abundance condition by a user abundance for the taxon in relation to a reference abundance range for the taxon, and satisfaction of an association type condition by an association, of the set of associations, between the taxon and the at least one microorganism-related condition, and determining the significance index metric for a user associated with the user sample, based on the set of labels. However, determining significance index metrics based on one or more labels can be determined in any suitable manner.

In a variation, determining one or more significance index metrics can be based on one or more artificial intelligence approaches (e.g., machine learning models; such as significance index models applying artificial intelligence approaches; etc.), such as to calculate a sample's probability of coming from a user with a certain microorganism-related condition of interest or being healthy. Determining one or more significance index metrics based on one or more artificial intelligence approaches can include any one or more of: transforming (e.g., centered log ratio transformation, isometric log ratio transformation; filtering such as in relation to feature selection for selecting features with greatest contribution to classification and/or improved output accuracy; applying any suitable machine learning algorithms (e.g., for training and/or processing types of machine learning models described herein; etc.); model selection (e.g., for selecting between different types of machine learning models, such as based on accuracy comparisons; etc.); applying machine learning models, such as to classify one or more components (e.g., samples), such as for classification of a sample (and/or user, etc.) as healthy or presenting one or more microorganism-related conditions; and/or other suitable processes. In a specific example, the method 100 can include performing one or more centered log ratio and/or isometric log ratio transformation of the abundance of microorganisms present in one or more samples; filtering datasets, such as to select only the features corresponding to the taxa with greatest contribution to classification of samples as either healthy or presenting a microorganism-related condition; performing a set of different artificial intelligence approaches (e.g., random forest classifiers, support vector machines, logistic regression, K-means, closest neighbors, etc.) and/or other suitable analytical techniques for training a machine learning model for classifying samples (e.g., novel samples) from users as either healthy or presenting a microorganism-related condition; and applying the one or more selected machine learning models, such as using user features (e.g., derived a microorganism sequence dataset generated based on a user sample; etc.) as inputs, for classifying one or more samples as either healthy or presenting a microorganism-related condition, based on the probability output by the machine learning model. In a specific example, the machine learning model can output a probability of belonging to either group (e.g., healthy or microorganism-related condition), where the significance index metric can be determined based on:

$$\text{Significance Index} = (\text{probability of being in the "microorganism-related condition" group}) \times 100$$

where the determined significance index metric can be used not just as a score of closeness to one or another group (e.g., healthy group or microorganism-related condition group, etc.), but additionally or alternatively as the probability of belonging to one category or another; and where the significance index metrics can be used to classify microbial samples as coming from healthy users or users with one or more microbial-related condition (e.g., performing or facilitating one or more diagnoses; etc.).

In a specific example, determining the significance index metric includes determining a microorganism-related condition classification associated with a health state of a user for the at least one microorganism-related condition, based on user microbiome composition features (e.g., user abundances for a set of taxa associated with one or more microorganism-related conditions; etc.) and a machine learning model derived from the set of associations and the set of reference abundance ranges (e.g., for the set of taxa associated with one or more microorganism-related conditions; etc.). In a specific example, determining the significance index metric includes determining a microorganism-related condition classification associated with a health state of the user for the at least one microorganism-related condition, based on the user microbiome composition features (e.g., user abundances for a set of taxa associated with one or more microorganism-related conditions; etc.) and a machine learning model derived from the set of associations and the set of reference microbiome composition features (e.g., reference abundance ranges for the set of taxa associated with one or more microorganism-related conditions; etc.).

Artificial intelligence approaches can be used to determine any suitable number and type of classifications, probabilities, and/or other suitable outputs, such as for determining any suitable types of significance index metrics (e.g., described herein, etc.). For example, machine learning models can be trained with any suitable number of labels for one or more microorganism-related conditions (e.g., labels of healthy and different severities of a condition; different labels for different conditions, where outputs of the model can include probabilities of presenting each of the different microorganism-related conditions; etc.).

Figure 14:
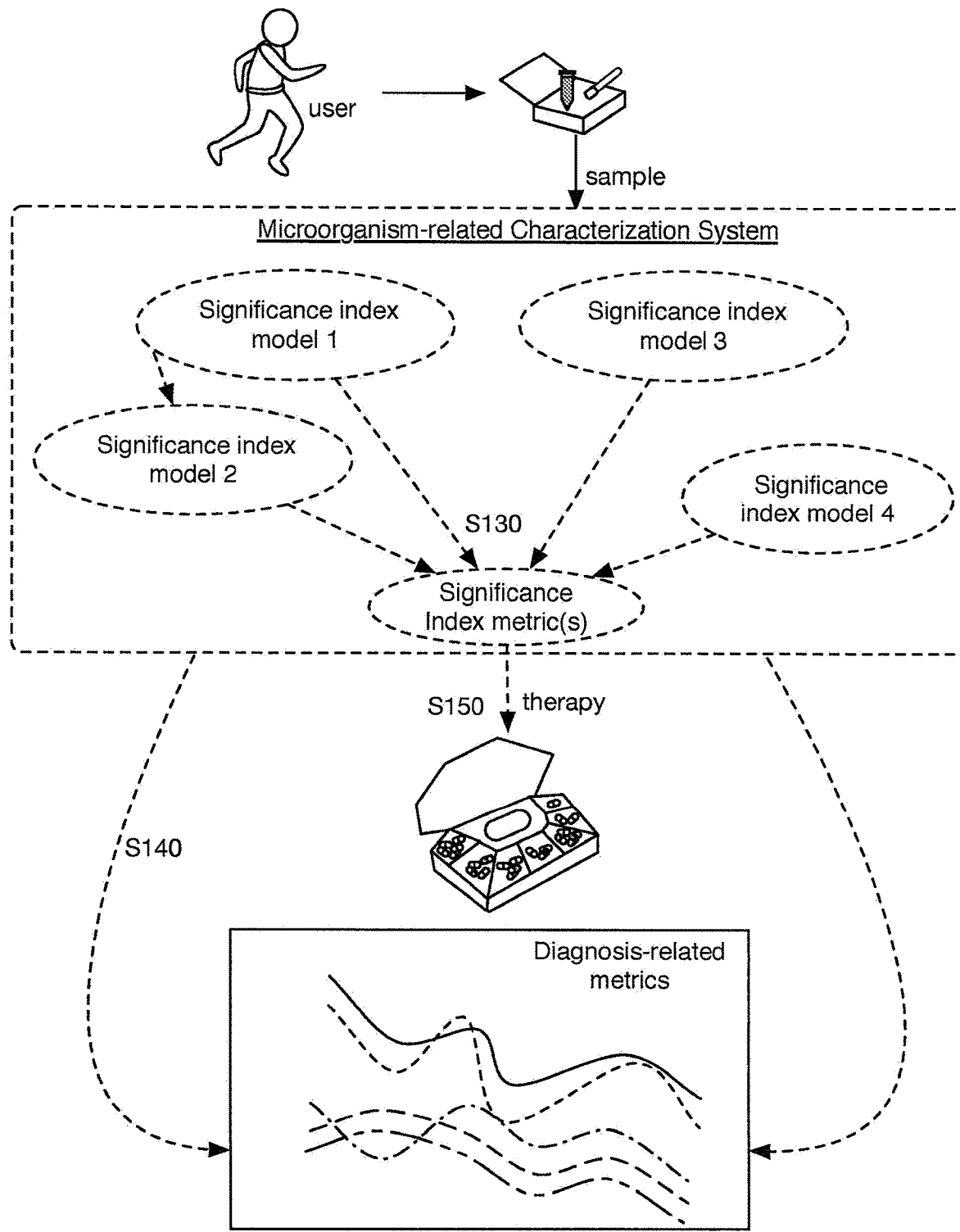
FIG. 14 includes a schematic representation of variations of an embodiment of the method.
Figure 15:
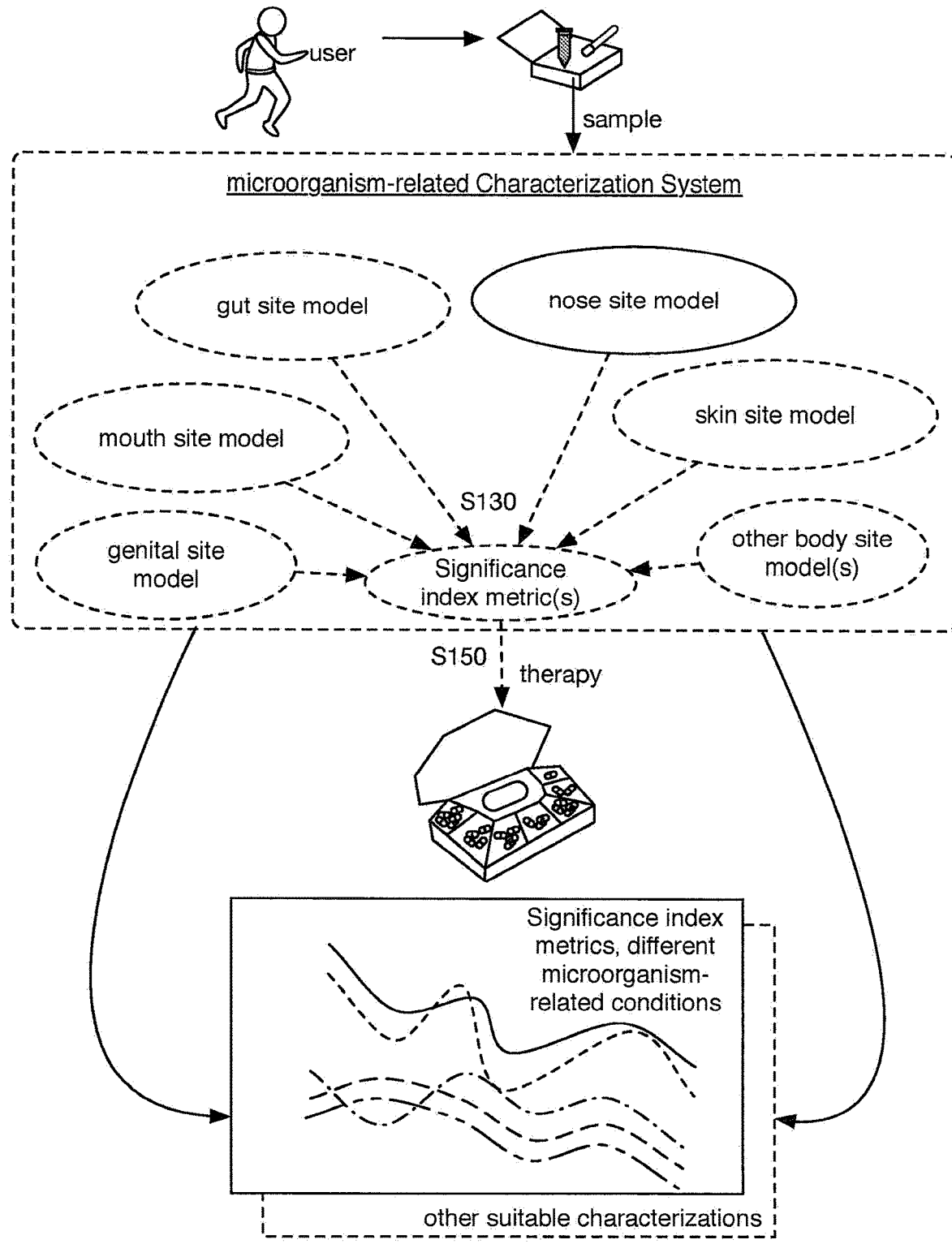
FIG. 15 includes a schematic representation of variations of an embodiment of the method.
Figure 16:
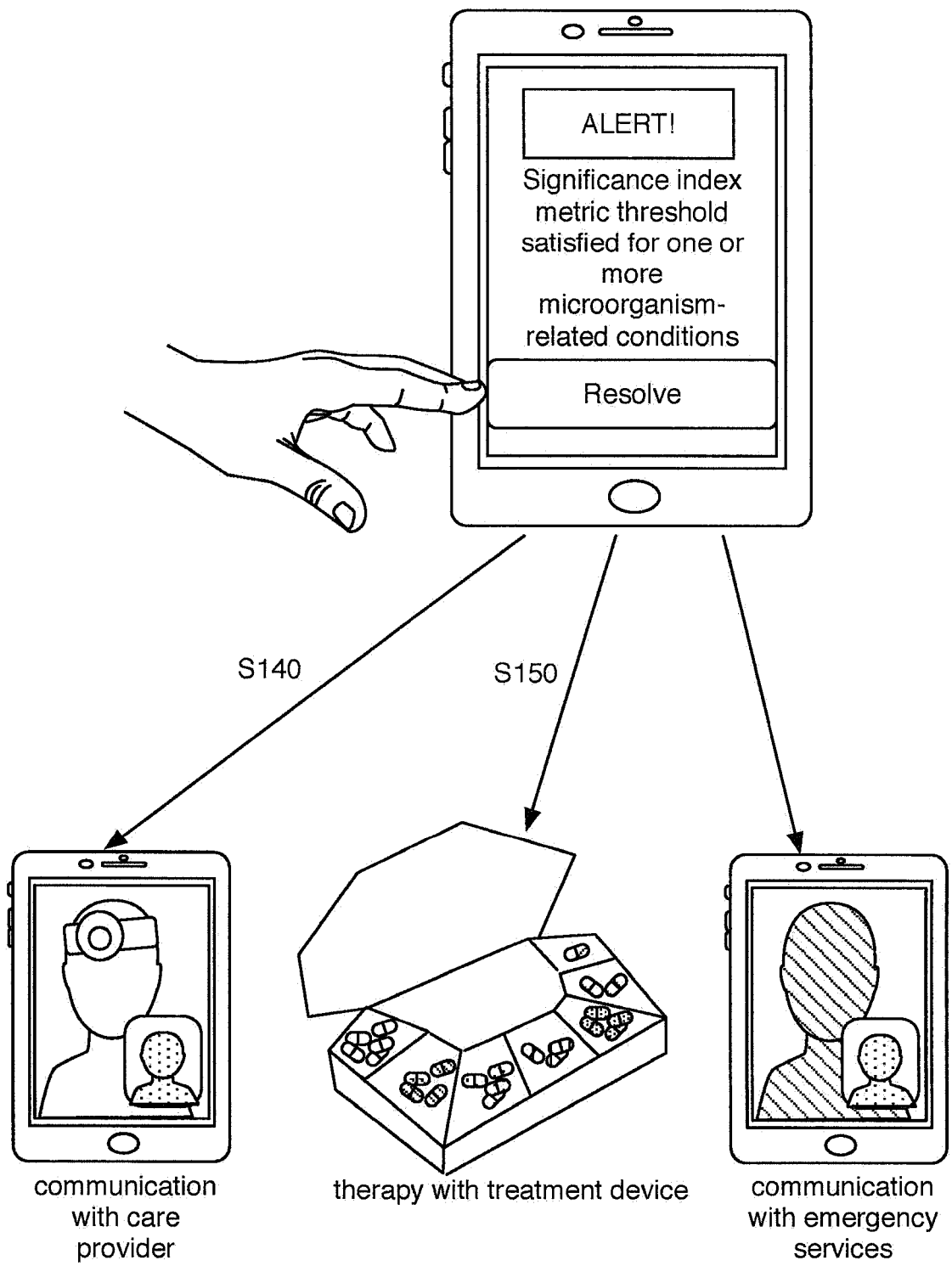
FIG. 16 includes a schematic representation of variations of an embodiment of the method.

Different significance index models (e.g, different combinations of significance index models; different models applying different analytical techniques; different inputs and/or output types; applied in different manners such as in relation to time and/or frequency; different significance index approaches, such as in relation to variants described herein, etc.) can be applied (e.g., executed, selected, retrieved, stored, trained, generated; as shown in FIG. 14-15, etc.) based on one or more of: microorganism-related conditions (e.g., using different significance index models depending on the microorganism-related condition or conditions being characterized, such as where different significance index models possess differing levels of suitability for processing data in relation to different microorganism-related conditions and/or combinations of conditions, etc.), taxa (e.g., using different significance index models depending on the types of taxa involved with determining significance index metrics, such as the types of taxa with associations to the relevant one or more microorganism-related conditions; etc.), users (e.g., different significance index models based on different user data and/or characteristics, demographic characteristics, genetics, environmental factors, etc.), microorganism-related characterizations (e.g., different significance index models for different types of characterizations, such as a therapy-related characterization versus a diagnosis-related characterization, such as for identifying a classification versus determining a propensity score for a microorganism-related condition; etc.), therapies (e.g., different significance index models for determining and/or monitoring efficacy of different therapies, etc.), body sites (e.g., different significance index models for processing microorganism datasets corresponding to biological samples from different sample collection sites; etc.), supplementary data (e.g., different models for predicting different types of user data, etc.), and/or any other suitable components. However, significance index models (e.g., as shown in FIG. 10) can be tailored and/or used in any suitable manner for facilitating significance index metric determination.

Additionally or alternatively, determining one or more significance index metrics S130 and/or any suitable portions of embodiments of the method 100 can employ any suitable combination of analytical techniques (e.g., in any suitable manner) described in U.S. application Ser. No. 16/047,840 filed 27 Jul. 2018, which is herein incorporated in its entirety by this reference. However, determining significance index metrics S130 can be performed in any suitable manner.

2.4 Facilitating Diagnosis.

Embodiments of the method 100 can additionally or alternatively include facilitating diagnosis of one or more microorganism-related conditions based on one or more significance index metrics (and/or associated data) S140, which can function to use significant index metrics and/or associated data to diagnose and/or aid in diagnosis of one or more microorganism-related conditions. In examples, calculated propensity scores, classifications (e.g., using machine learning models), sets of assigned labels, and/or other suitable significance index metrics and/or associated data can be used in diagnosis. In an example, the method 100 can include facilitating diagnosis of the user for the at least one microorganism-related condition based on the significance index metric.

Facilitating diagnosis can include using significance index metrics in an additional or alternative manner to using other suitable diagnostic data (e.g., supplementary data provided by a user; etc.) and/or diagnostic procedures (e.g., computed tomography (CT scan), ultrasound, biopsy, blood test, cancer screening exams, urine test diagnostic imaging, other suitable diagnostic procedures associated with microorganism-related conditions, survey-related information, and/or any other suitable test, etc.). In a specific example, facilitating diagnosis can include recommending a user to undergo one or more diagnostic procedures and/or to request additional diagnostic-related data, such as based on one or more conditions (e.g., conditions indicating a likelihood of presenting one or more microorganism-related conditions, etc.). In specific examples, diagnosis, recommending additional diagnostic procedures, and/or requesting additional diagnostic-related data can be in response to a calculated propensity score satisfying a threshold condition; a number of assigned labels (e.g., "flags") to taxa satisfying a threshold condition; or a probability output (e.g., corresponding to a classification) satisfying a threshold condition. Additionally or alternatively, threshold conditions and/or other suitable types of conditions can be used in any suitable manner for any suitable portions of embodiments of the method 100. However, using significance index metrics with one or more other processes can be performed in any suitable manner.

Facilitating diagnosis S140, facilitating therapeutic intervention S150, and/or other suitable portions of embodiments of the method 100 can be based on (e.g., can use as inputs into a model, can user as inputs into calculations; etc.) one or more features (e.g., described herein; determined in relation to S120; user features; reference features; supplementary features; etc.), and/or any other suitable data.

Facilitating diagnosis can include any one or more of: providing a diagnosis; providing a diagnostic recommendation (e.g., to seek a care provider to perform a diagnostic procedure; etc.); transmitting significance index metrics and/or other associated data to one or more entities (e.g., care providers, for use by care providers in performing a diagnosis; etc.); providing reports to users (e.g., at user devices; etc.); and/or any other suitable diagnostic-related processes.

Facilitating diagnosis can include facilitating detection of microorganism-related conditions for a user, which can motivate subsequent promotion of therapies, such as for modulation of a user microbiome for improving a user health state associated with one or more microorganism-related conditions (e.g., modulation of a user microbiome towards healthy abundance ranges for taxa associated with the one or more microorganism-related conditions; etc.). Additionally or alternatively, diagnostic procedures can include any one or more of: medical history analyses, imaging examinations, cell culture tests, antibody tests, skin prick testing, patch testing, blood testing, challenge testing, performing portions of embodiments of the method 100, and/or any other suitable procedures for facilitating the detecting (e.g., observing, predicting, etc.) of microorganism-related conditions. Additionally or alternatively, diagnostic device-related information and/or other suitable diagnostic information can be processed in relation to facilitating diagnosis and/or therapeutic intervention, and/or collected, used, and/or otherwise processed in relation to any suitable portions of embodiments of the method 100.

2.5 Facilitating Therapeutic Intervention.

Embodiments of the method 100 can additionally or alternatively include facilitating therapeutic intervention for the one or more microorganism-related conditions (e.g., based on the one or more significance index metrics and/or associated data, etc.) S150, which can function to use significant index metrics and/or associated data to facilitate therapeutic intervention (e.g., promote therapies, provide therapies, etc.), such as for improving a health state of a user in relation to one or more microorganism-related conditions. In an example, the method 100 can include facilitating therapeutic intervention for the user for the at least one microorganism-related condition based on the significance index metric.

Facilitating therapeutic intervention can include identifying, selecting, ranking, prioritizing, predicting, discouraging, and/or otherwise facilitating therapeutic intervention. For example, facilitating therapeutic intervention can include determining one or more of probiotic-based therapies, bacteriophage-based therapies, small molecule-based therapies, and/or other suitable therapies, such as therapies that can shift a subject's microbiome composition, function, diversity, and/or other characteristics (e.g., microbiomes at any suitable sites, etc.) toward a desired state (e.g., equilibrium state, etc.), such as a towards a healthy microbiome composition (e.g., abundances in healthy reference abundance ranges; etc.), such as in promotion of a user's health, such as for modifying a state of one or more microorganism-related conditions, and/or for other suitable purposes.

Therapies (e.g., microorganism-related therapies, etc.) can include any one or more of: consumables (e.g., probiotic therapies, prebiotic therapies, medication such as antibiotics, allergy or cold medication, bacteriophage-based therapies, consumables for underlying conditions, small molecule therapies, etc.); device-related therapies (e.g., monitoring devices; sensor-based devices; medical devices; implantable medical devices; etc.); surgical operations; psychological-associated therapies (e.g., cognitive behavioral therapy, anxiety therapy, talking therapy, psychodynamic therapy, action-oriented therapy, rational emotive behavior therapy, interpersonal psychotherapy, relaxation training, deep breathing techniques, progressive muscle relaxation, meditation, etc.); behavior modification therapies (e.g., physical activity recommendations such as increased exercise; dietary recommendations such as reducing sugar intake, increased vegetable intake, increased fish intake, decreased caffeine consumption, decreased alcohol consumption, decreased carbohydrate intake; smoking recommendations such as decreasing, tobacco intake; weight-related recommendations; sleep habit recommendations etc.); topical administration therapies (e.g., topical probiotic, prebiotic, and/or antibiotics; bacteriophage-based therapies); environmental factor modification therapies; modification of any other suitable aspects associated with one or more microorganism-related conditions; and/or any other suitable therapies (e.g., for improving a health state associated with one or more microorganism-related conditions, such as therapies for improving one or more microorganism-related conditions, therapies for reducing the risk of one or more microorganism-related conditions, etc.). In examples, types of therapies can include any one or more of: probiotic therapies, bacteriophage-based therapies, small molecule-based therapies, cognitive/behavioral therapies, physical rehabilitation therapies, clinical therapies, medication-based therapies, diet-related therapies, and/or any other suitable therapy designed to operate in any other suitable manner in promoting a user's health.

In variations, therapies can include site-specific therapies associated with one or more body sites, such as for facilitating modification of microbiome composition and/or function at one or more different body sites of a user (e.g., one or more different collection sites, etc.), such as targeting and/or transforming microorganisms associated with one or more of a nose site, gut site, skin site, mouth site, and/or genital site; such as by facilitating therapeutic intervention in relation to one or more therapies configured to specifically target one or more user body sites, such as microbiome at one or more of the user body sites; such as for facilitating improvement of one or more microorganism-related conditions (e.g., by modifying user microbiome composition and/or function at a particular user body site towards a target microbiome composition and/or function, such as microbiome composition and/or function at a particular body site and associated with a healthy microbiome status and/or lack of the one or more microorganism-related condition; etc.). Facilitating therapeutic intervention in relation to site-specific therapies can be based on site-specific significance index metrics (e.g., facilitating a site-specific therapy to modulate a microbiome composition at a specific site towards a healthy microbiome composition including taxa used in determining a corresponding site-specific significance index metric, such as taxa associated with the relevant microorganism-related condition at the site; etc.). Site-specific therapies can include any one or more of consumables (e.g., targeting a body site microbiome and/or microbiomes associated with any suitable body sites; etc.); topical therapies (e.g., for modifying a skin microbiome, a nose microbiome, a mouth microbiome, a genitals microbiome, etc.); and/or any other suitable types of therapies. In an example, the method 100 can include collecting a sample associated with a first body site (e.g., including at least one of a nose site, gut site, a skin site, a genital site, a mouth site, etc.) from a user; determining site-specific composition features associated with the first body site; determining a significance index metric for the user for the microorganism-related condition based on the site-specific composition features (e.g., and site-specific reference features; etc.); and facilitating therapeutic intervention in relation to a first site-specific therapy for the user (e.g., providing the first site-specific therapy to the user; etc.) for facilitating improvement of the microorganism-related condition, based on the significance index metric, where the first site-specific therapy is associated with the first body site. In an example, the method 100 can include collecting a post-therapy sample from the user after the facilitation of the therapeutic intervention in relation to the first site-specific therapy (e.g., after the providing of the first site-specific therapy; etc.), where the post-therapy sample is associated with a second body site (e.g., including at least one of the nose site, gut site, the skin site, the genital site, the mouth site; etc.); determining a post-therapy significance index metric for the user for the microorganism-related condition based on site-specific features associated with the second body site; and facilitating therapeutic intervention in relation to a second site-specific therapy for the user (e.g., providing a second site-specific therapy to the user; etc.) for facilitating improvement of the microorganism-related condition, based on the post-therapy significance index metric, where the second site-specific therapy is associated with the second body site. However, significance index metrics (e.g., site-specific or site-independent) can be determined and/or used at any suitable time and frequency (e.g., pre-therapy, post-therapy, at any suitable stage of a user's microbiome; at any suitable temporal indicator; etc.).

In a variation, therapies can include one or more bacteriophage-based therapies (e.g., in the form of a consumable, in the form of a topical administration therapy, etc.), where one or more populations (e.g., in terms of colony forming units) of bacteriophages specific to a certain bacteria (or other microorganism) represented in the subject can be used to down-regulate or otherwise eliminate populations of the certain bacteria. As such, bacteriophage-based therapies can be used to reduce the size(s) of the undesired population(s) of bacteria represented in the subject. Additionally or alternatively, bacteriophage-based therapies can be used to increase the relative abundances of bacterial populations not targeted by the bacteriophage(s) used. However, bacteriophage-based therapies can be used to modulate characteristics of microbiomes (e.g., microbiome composition, microbiome function, etc.) in any suitable manner, and/or can be used for any suitable purpose.

In variations, therapies can include one or more probiotic therapies and/or prebiotic therapies associated with any combination of at least one or more of (e.g., including any combination of one or more of, at any suitable amounts and/or concentrations, such as any suitable relative amounts and/or concentrations; etc.) any suitable taxa described herein (e.g., in relation to one or more microbiome composition features associated with one or more microorganism-related conditions, etc.), and/or any other suitable microorganisms associated with any suitable taxonomic groups (e.g., microorganisms from taxa described herein, such as in relation to microbiome features; taxa associated with functional features described herein, etc.). For one or more probiotic therapies and/or other suitable therapies, microorganisms associated with a given taxonomic group, and/or any suitable combination of microorganisms can be provided at dosages of 0.1 million to 10 billion CFU, and/or at any suitable amount (e.g., as determined from a therapy model that predicts positive adjustment of a patient's microbiome in response to the therapy; different amounts for different taxa; same or similar amounts for different taxa; etc.). In an example, a subject can be instructed to ingest capsules including the probiotic formulation according to a regimen tailored to one or more of his/her: physiology (e.g., body mass index, weight, height), demographic characteristics (e.g., gender, age), severity of dysbiosis, sensitivity to medications, and any other suitable factor. In examples, probiotic therapies and/or prebiotic therapies can be used to modulate a user microbiome (e.g., in relation to composition, function, etc.) for facilitating improvement of one or more microorganism-related conditions. In examples, facilitating therapeutic intervention can include promoting (e.g., recommending, informing a user regarding, providing, administering, facilitating obtainment of, etc.) one or more probiotic therapies and/or prebiotic therapies to a user, such as for facilitating improvement of one or more microorganism-related conditions.

In a specific example of probiotic therapies, as shown in FIG. 11, candidate therapies can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis. However, probiotic therapies and/or prebiotic therapies can be configured in any suitable manner.

In another specific example, therapies can include medical-device based therapies (e.g., associated with human behavior modification, associated with treatment of disease-related conditions, etc.).

Additionally or alternatively, facilitating therapeutic intervention can be based on identification of a "normal" or baseline microbiome composition and/or functional features, as assessed from subjects of a population of subjects who are identified to be in good health. Upon identification of a subset of subjects of the population of subjects who are characterized to be in good health (e.g., using features of the characterization process), therapies that modulate microbiome compositions and/or functional features toward those of subjects in good health (e.g., using significance index metrics; etc.) can be determined and/or promoted. Therapies can additionally or alternatively include therapies that can shift microbiomes of subjects who are in a state of dysbiosis toward one of the identified baseline microbiome compositions and/or functional features.

Microorganism compositions associated with probiotic therapies and/or prebiotic therapies (e.g., associated with probiotic therapies, such as determined based on one or more significance index metrics, etc.) can include microorganisms that are culturable (e.g., able to be expanded to provide a scalable therapy) and/or non-lethal (e.g., non-lethal in their desired therapeutic dosages). Furthermore, microorganism compositions can include a single type of microorganism that has an acute or moderated effect upon a subject's microbiome. Additionally or alternatively, microorganism compositions can include balanced combinations of multiple types of microorganisms that are configured to cooperate with each other in driving a subject's microbiome toward a desired state. For instance, a combination of multiple types of bacteria in a probiotic therapy can include a first bacteria type that generates products that are used by a second bacteria type that has a strong effect in positively affecting a subject's microbiome. Additionally or alternatively, a combination of multiple types of bacteria in a probiotic therapy can include several bacteria types that produce proteins with the same functions that positively affect a subject's microbiome.

Probiotic and/or prebiotic compositions can be naturally or synthetically derived. For instance, in one application, a probiotic composition can be naturally derived from fecal matter or other biological matter (e.g., of one or more subjects having a baseline microbiome composition and/or functional features, as identified using one or more processes of embodiments of the method 100; etc.). Additionally or alternatively, probiotic compositions can be synthetically derived (e.g., derived using a benchtop method) based upon a baseline microbiome composition and/or functional features. In variations, microorganism agents that can be used in probiotic therapies can include one or more of: yeast (e.g., *Saccharomyces boulardii*), gram-negative bacteria (e.g., *E. coli* Nissle), gram-positive bacteria (e.g., *Bifidobacteria bifidum, Bifidobacteria infantis, Lactobacillus rhamnosus, Lactococcus lactis, Lactobacillus plantarum, Lactobacillus acidophilus, Lactobacillus casei, Bacillus polyfermenticus*, etc.), and any other suitable type of microorganism agent. However, probiotic therapies, prebiotic therapies and/or other suitable therapies can include any suitable combination of microorganisms associated with any suitable taxa described herein, and/or therapies can be configured in any suitable manner.

In variations, facilitating therapeutic intervention (e.g., providing therapies, etc.) and/or other suitable portions of embodiments of the method 100 can include provision of notifications (e.g., as shown in FIGS. 8A-8D, 12, and 16) to a user regarding one or more recommended therapies, other forms of therapy, significance index metrics, diagnoses, diagnostic recommendations, and/or any other suitable data (e.g., described herein; etc.). In a specific example, facilitating therapeutic intervention (e.g., providing a therapy; etc.) can include providing therapy recommendations (e.g., substantially concurrently, such as in the same report, as providing significance index metrics and/or data derived from significance index metrics; etc.) and/or other suitable therapy-related information (e.g., therapy efficacy; comparisons to other individual users, subgroups of users, and/or populations of users; therapy comparisons; historic therapies and/or associated therapy-related information; psychological therapy guides such as for cognitive behavioral therapy; etc.). Notifications can be presented a web interface (e.g., through a user account associated with and identifying a user; etc.).

Notifications can be provided to a user by way of an electronic device (e.g., personal computer, mobile device, tablet, wearable, head-mounted wearable computing device, wrist-mounted wearable computing device, etc.), such as a device that executes an application, web interface, and/or messaging client configured for notification provision. In one example, a web interface of a personal computer or laptop associated with a user can provide access, by the user, to a user account of the user, where the user account can be associated with information regarding the user's microbiome (e.g., detailed characterization of aspects of the user's microbiome in relation to correlations with microorganism-related conditions; etc.), and/or notifications regarding suggested therapeutic measures (e.g., generated in Blocks S140 and/or S170, etc.). In another example, an application executing at a personal electronic device (e.g., smart phone, smart watch, head-mounted smart device) can be configured to provide notifications (e.g., at a display, haptically, in an auditory manner, etc.), such as regarding therapy suggestions based on significance index metrics. Notifications and/or probiotic therapies can additionally or alternatively be provided directly through an entity associated with a user (e.g., a caretaker, a spouse, a significant other, a healthcare professional, etc.). In variations, notifications can additionally or alternatively be provided to an entity (e.g., healthcare professional) associated with a user, such as where the entity is able to facilitate provision of the therapy (e.g., by way of prescription, by way of conducting a therapeutic session, through a digital telemedicine session using optical and/or audio sensors of a computing device, etc.). Providing notifications and/or otherwise facilitating therapeutic intervention, however, be performed in any suitable manner.

However, facilitating therapeutic intervention S150 can be performed in any suitable manner.

3. Examples.

Figure 7A:
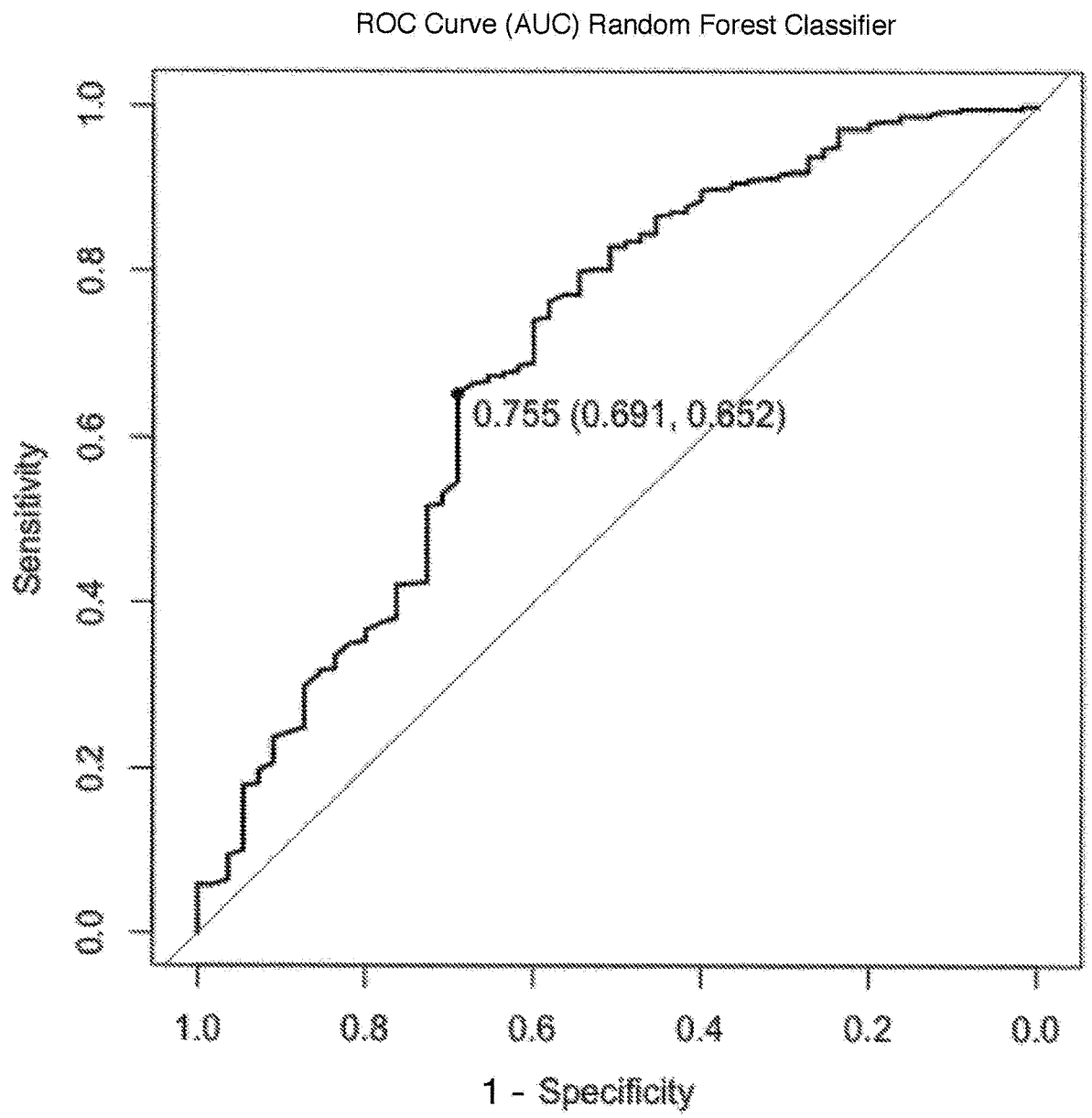
FIG. 7A-7E include graph representations of metrics for caffeine consumer prediction machine learning models in a variation of an embodiment of a method.
Figure 7B:
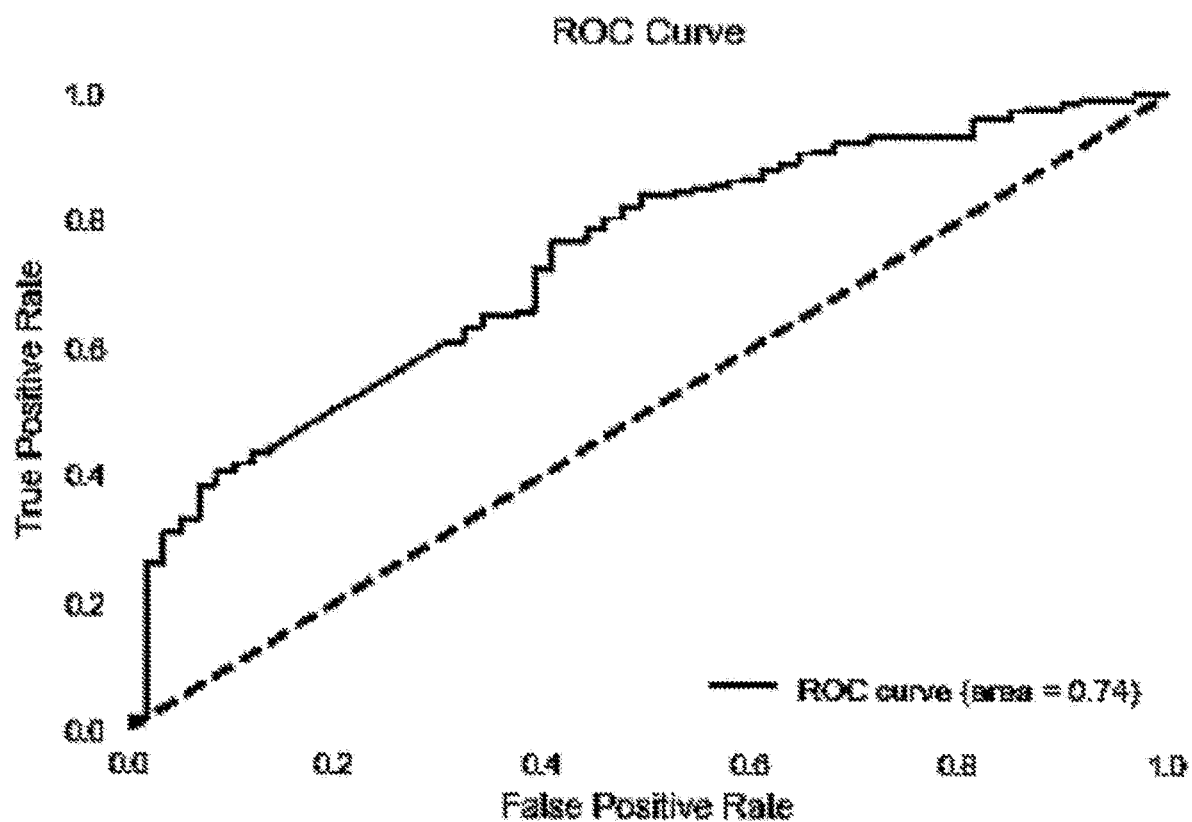
Figure 7C:
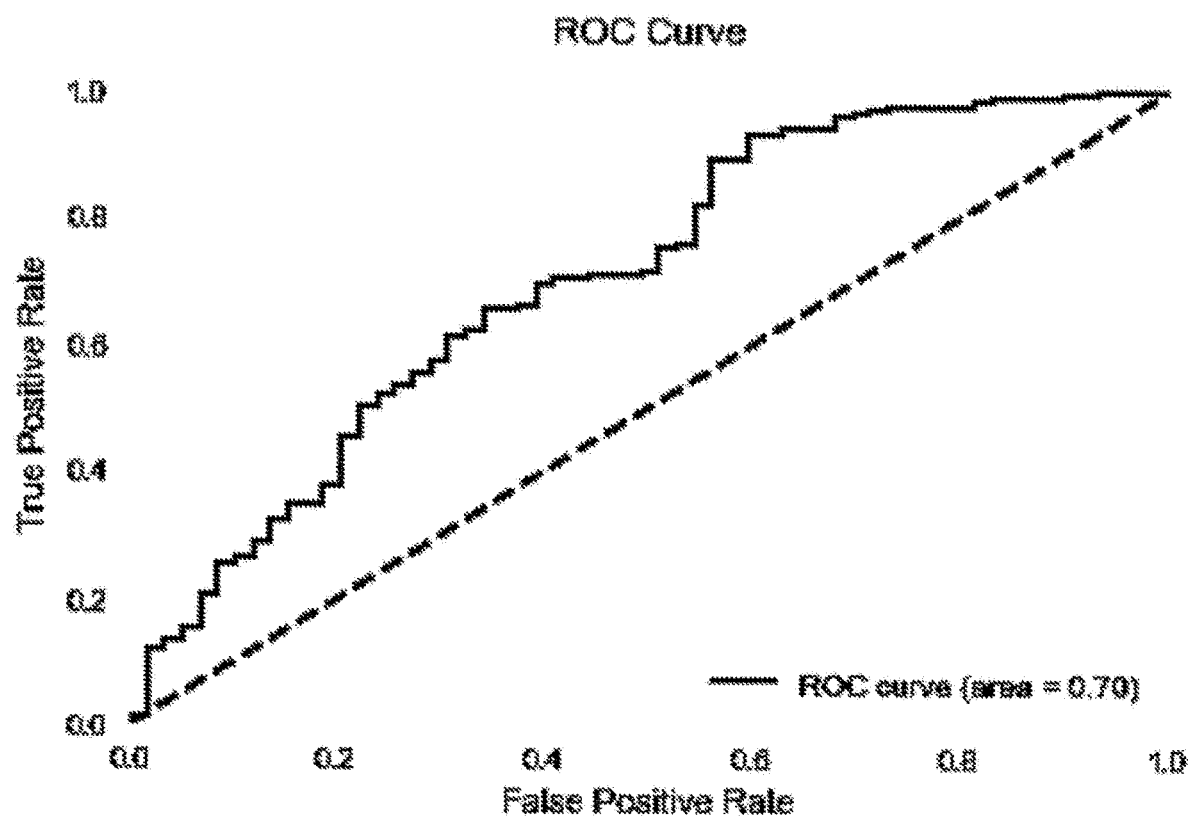
Figure 7D:
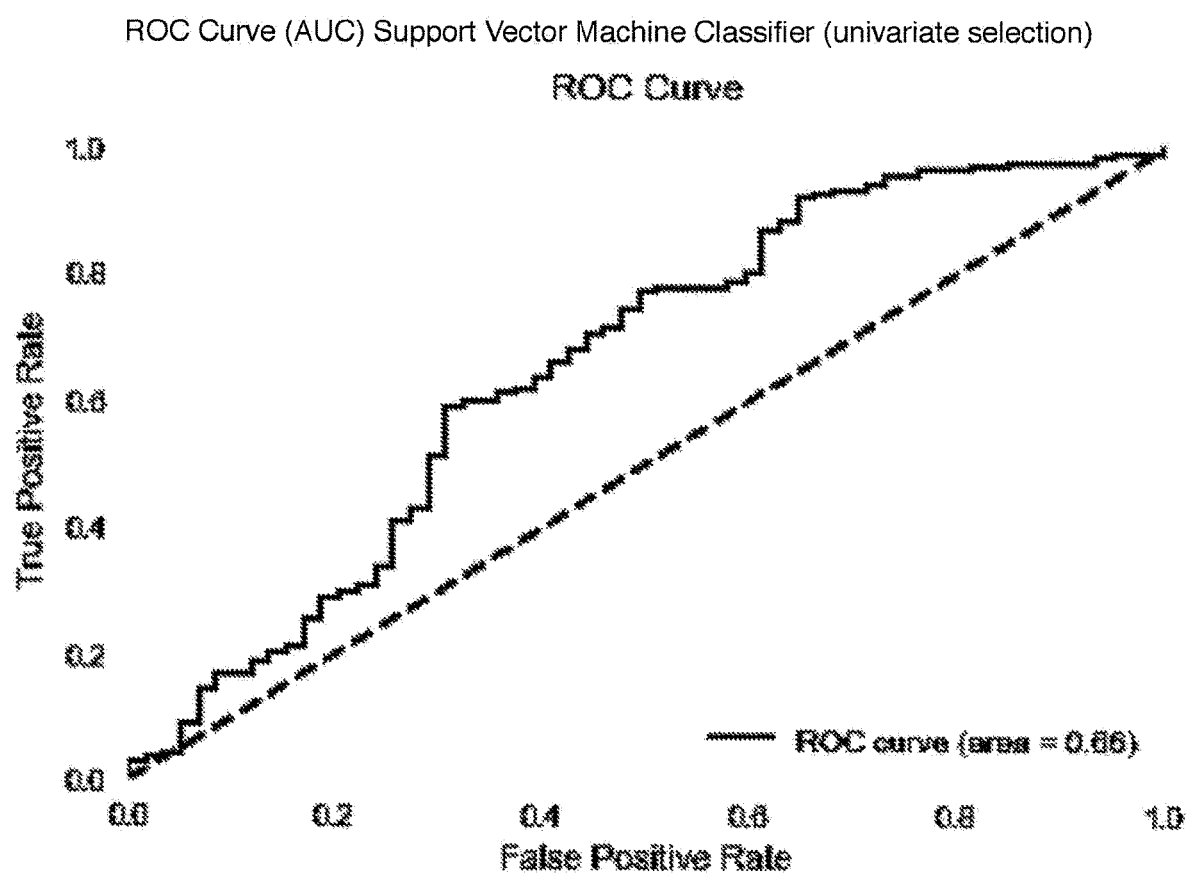
Figure 7E:
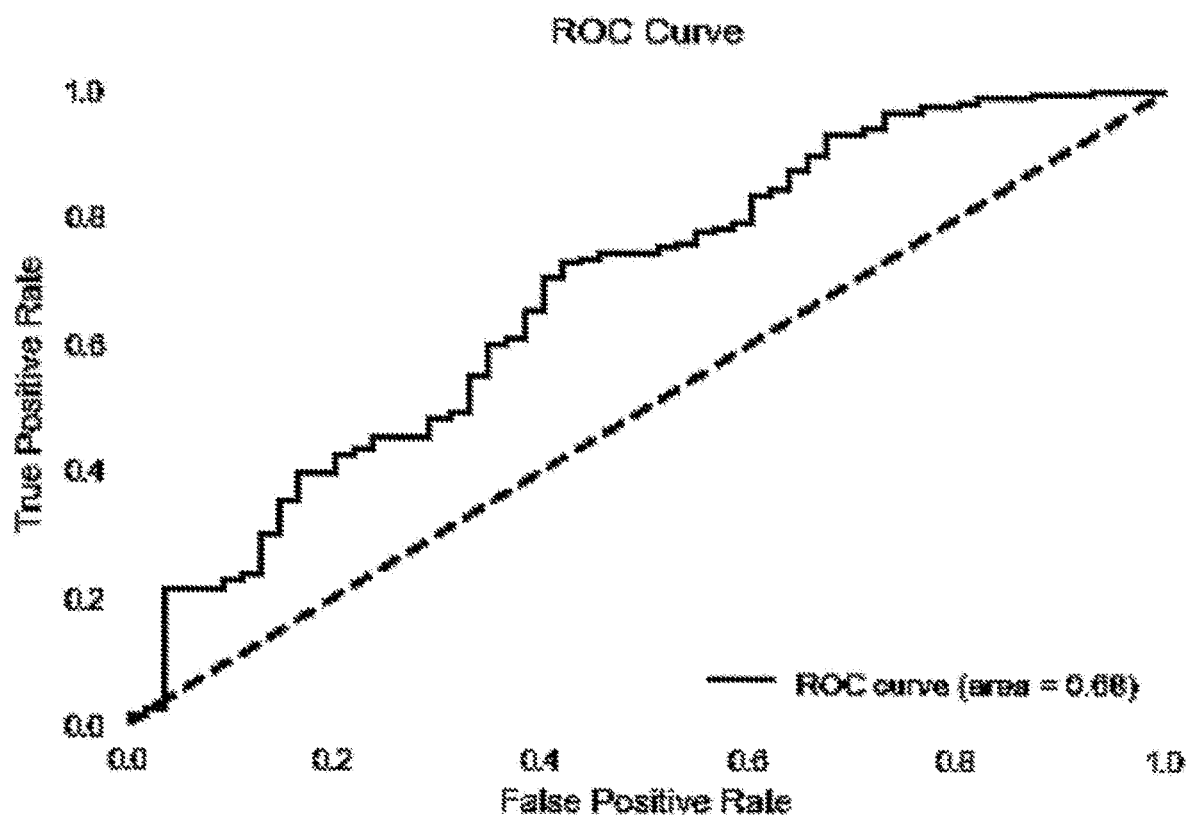
Figure 9:
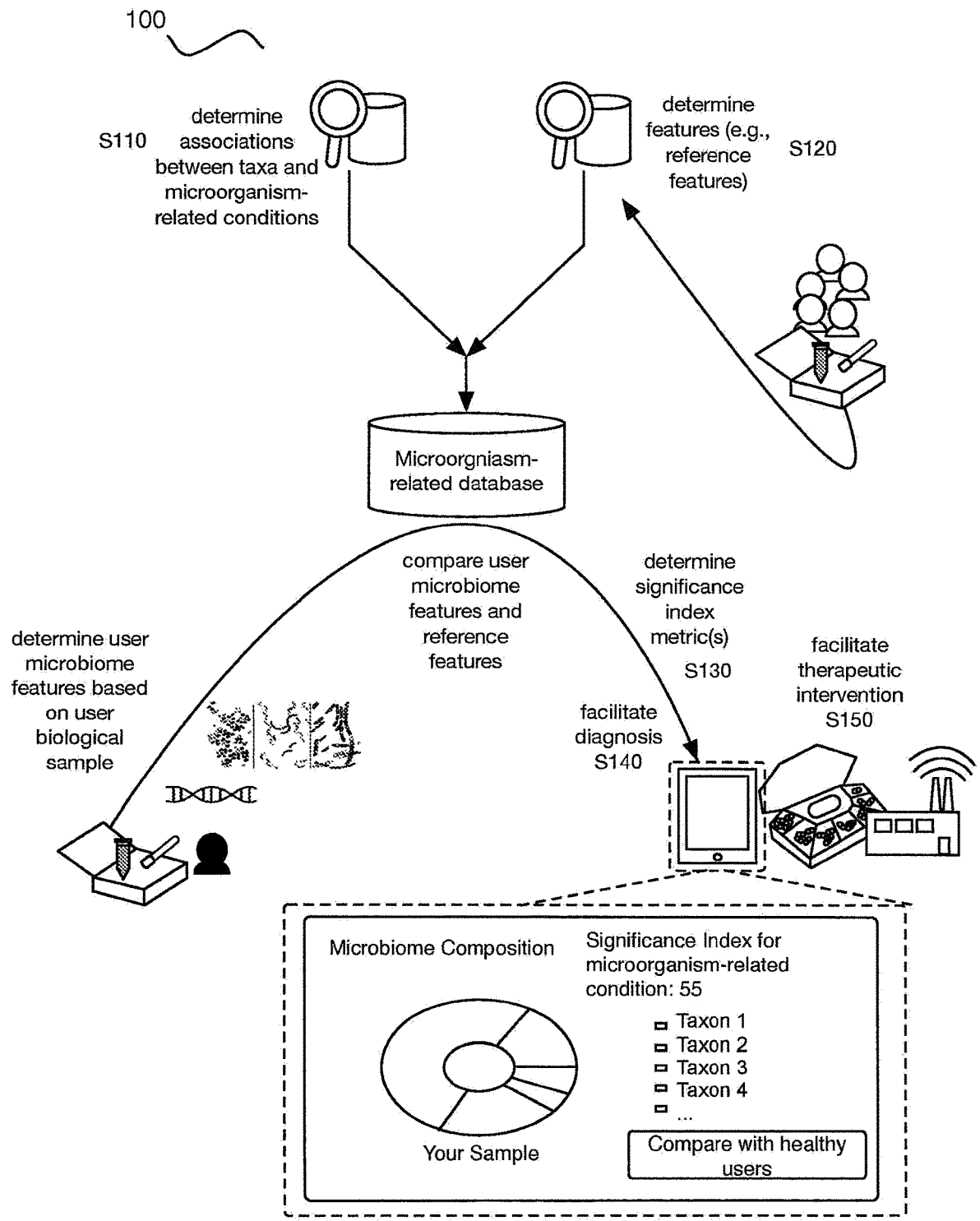
FIG. 9 includes a schematic representation of variations of an embodiment of the method.
Figure 12:
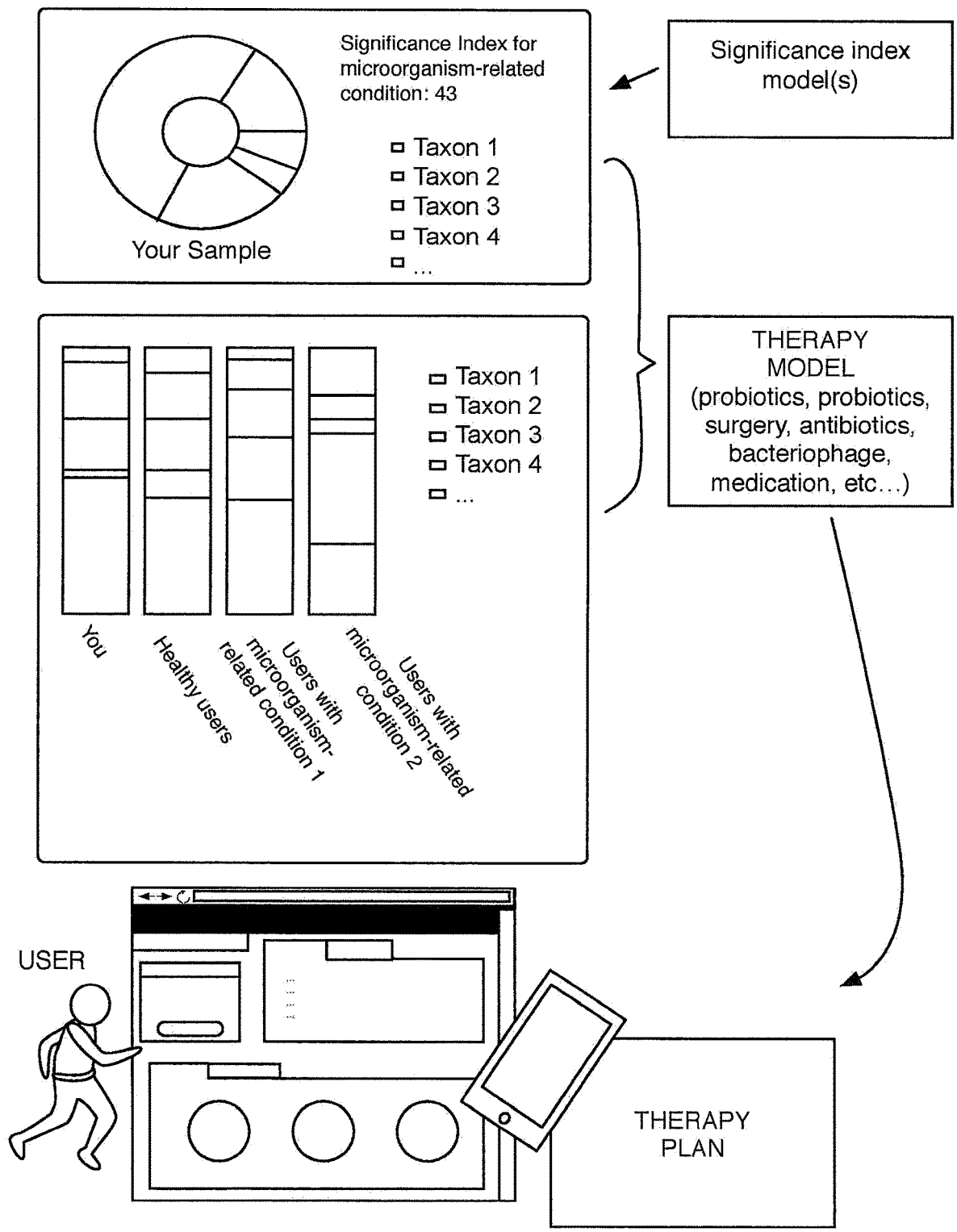
FIG. 12 includes a schematic representation of variations of an embodiment of the method.

In specific examples, one or more diet-related condition models (e.g., for determining diet-relation condition classifications such as whether a user consumes a certain food or drink, follows a certain diet, etc.), such as a caffeine consumption model (e.g., and/or other suitable significance index models and/or related models; and/or other suitable models for any suitable diet-related conditions, such as described herein, etc.) can be processed (e.g., generated, trained, applied, etc.), such as for predicting, based on set of microbiome composition features (e.g., user microbiome composition features such as user abundances for taxa associated with caffeine consumption, etc.) and/or other suitable features (e.g., supplementary features, microbiome functional features, etc.) a diet-related condition metric, such as a caffeine consumption metric (e.g., a classification as to whether the user is a caffeine consumer or not, etc.). In specific examples, taxa (and/or associated abundances) can be associated with one or more diet-related conditions (e.g., dietary profiles; types of consumed foods; etc.), such as where the taxa can additionally or alternatively be associated with one or more other microorganism-related conditions (e.g., disease; etc.), such as where determination of a diet's effect on microbiome can enable inferences and/or other suitable insights into a microbiome, a status of a microorganism-related condition, and/or other suitable microbiome and/or microorganism-related condition insights, such as in relation to diagnostics and/or therapeutics. In a specific example, a caffeine consumer model can be trained upon and/or otherwise processed based on features describing taxa abundances for caffeine consumers and non-caffeine consumers. In a specific example, different artificial intelligence approaches can be applied for training different machine learning models, such as including support vector machine (SVM) models (e.g., as shown in FIG. 7B-7E) and/or random forest classifier models (e.g., as shown in FIG. 7A). In specific examples, microbiome composition features (and/or other suitable microbiome features) for caffeine consumer prediction (e.g., for processing caffeine consumer models; etc.) and/or other suitable diet-related condition predictions (e.g., classifications, etc.) can be associated with one or more taxa including: *Alistipes; Anaerotruncus; Bacteroides; Bifidobacterium; Bilophila; Blautia; Butyricimonas; Clostridium; Collinsella; Erysipelatoclostridium; Faecalibacterium; Flavobacterium; Flavonifractor; Granulicatella; Hespellia; Intestinimonas; Kluyvera; Lachnospira; Marvinbryantia; Odoribacter; Oscillibacter; Parabacteroides; Phascolarctobacterium; Pseudobutyrivibrio; Roseburia; Streptococcus; Subdoligranulum; Sutterella;* and/or *Terrisporobacter.* In a specific example, taxa for microbiome composition features can be selected through any suitable means, such as based on "importance score" in random forest approaches. In a specific example, determining the microorganism-related condition classification includes determining a caffeine consumption classification for the user based on the machine learning model and the user microbiome composition features associated with the set of microorganism taxa, where the set of microorganism taxa includes at least one of: *Alistipes; Anaerotruncus; Bacteroides; Bifidobacterium; Bilophila; Blautia; Butyricimonas; Clostridium; Collinsella; Erysipelatoclostridium; Faecalibacterium; Flavobacterium; Flavonifractor; Granulicatella; Hespellia; Intestinimonas; Kluyvera; Lachnospira; Marvinbryantia; Odoribacter; Oscillibacter; Parabacteroides; Phascolarctobacterium; Pseuclobutyrivibrio; Roseburia; Streptococcus; Subdoligranulum; Sutterella;* and *Terrisporobacter.* In a specific example, determining the microorganism-related condition classification includes determining a diet-related condition classification, associated with a diet-related condition, for the user based on the machine learning model and the user microbiome composition features associated with the set of microorganism taxa. In a specific example, the diet-related condition can include at least one of caffeine consumption, alcohol consumption, artificial sweetener consumption, and sugar consumption; where determining the microorganism-related condition classification comprises determining at least one of a caffeine consumption classification, an alcohol consumption classification, an artificial sweetener consumption classification, and a sugar consumption classification.

In specific examples, one or more significance index metrics can be determined for one or more HPV conditions and/or any suitable women's health-related conditions (e.g., described herein; as shown in FIG. 8A-8D), such as for characterizing how a user's vaginal microbiome composition is similar to or departs from that of healthy individuals without one or more of the women's health-related conditions.

Microbiome analysis can enable accurate and/or efficient microorganism-related characterization (e.g., of a user microbiome, of a user sample, of a user, etc.) and/or therapy provision (e.g., according to portions of embodiments of the method 100, etc.) for microorganism-related conditions caused by, correlated with, and/or otherwise associated with microorganisms, such as through determination and/or use of significance index metrics. Specific examples of the technology can overcome several challenges faced by conventional approaches. First, conventional approaches can require patients to visit one or more care providers to receive a characterization and/or a therapy recommendation, such as for a microorganism-related condition, which can amount to inefficiencies and/or health-risks associated with the amount of time elapsed before diagnosis and/or treatment, with inconsistency in healthcare quality, and/or with other aspects of care provider visitation. Second, conventional genetic sequencing and analysis technologies for human genome sequencing can be incompatible and/or inefficient when applied to the microbiome (e.g., where the human microbiome can include over 10 times more microbial cells than human cells; where viable analytical techniques and the means of leveraging the analytical techniques can differ; where optimal sample processing techniques can differ, such as for reducing amplification bias; where different approaches to microorganism-related characterizations can be employed; where the types of conditions and correlations can differ; where causes of the associated conditions and/or viable therapies for the associated conditions can differ; where sequence reference databases can differ; where the microbiome can vary across different body regions of the user such as at different collection sites; etc.). Third, the onset of sequencing technologies (e.g., next-generation sequencing, associated technologies, etc.) has given rise to technological issues (e.g., data processing and analysis issues for the plethora of generated sequence data; issues with processing a plurality of biological samples in a multiplex manner; information display issues; therapy prediction issues; therapy provision issues, etc.) that would not exist but for the unprecedented advances in speed and data generation associated with sequencing genetic material. Specific examples of the method 100 and/or system 200 can confer technologically-rooted solutions to at least the challenges described above.

First, specific examples of the technology can transform entities (e.g., users, biological samples, therapy facilitation systems including medical devices, etc.) into different states or things. For example, the technology can transform a biological sample into components able to be sequenced and analyzed to generate significance index metrics, such as usable for characterizing users in relation to one or more microorganism-related conditions (e.g., such as through use of next-generation sequencing systems, multiplex amplification operations; etc.). In another example, the technology can identify, discourage and/or promote (e.g., present, recommend, provide, administer, etc.), therapies (e.g., personalized therapies based on a microorganism related characterization; etc.) and/or otherwise facilitate therapeutic intervention (e.g., facilitating modification of a user's microbiome composition, microbiome functionality, etc.), such as based on significance index metrics, which can prevent and/or ameliorate one or more microorganism-related conditions, such as thereby transforming the microbiome and/or health of the patient (e.g., improving a health state associated with a microorganism-related condition; etc.), such as based on applying one or more microbiome features (e.g., applying correlations, relationships, and/or other suitable associations between microbiome features and one or more microorganism-related conditions; etc.). In another example, the technology can transform microbiome composition and/or function at one or more different body sites of a user (e.g., one or more different collection sites; etc.), such as targeting and/or transforming microorganisms associated with the nose, gut, skin, mouth, genitals, and/or other sites associated with a microbiome (e.g., by facilitating therapeutic intervention in relation to one or more site-specific therapies; etc.). In another example, the technology can control therapy facilitation systems (e.g., dietary systems; automated medication dispensers; behavior modification systems; diagnostic systems; disease therapy facilitation systems; etc.) to promote therapies (e.g., by generating control instructions for the therapy facilitation system to execute; etc.), thereby transforming the therapy facilitation system.

Second, specific examples of the technology can confer improvements in computer-related technology (e.g., improving computational efficiency in storing, retrieving, and/or processing microorganism-related data for microorganism-related conditions such as associations and/or features; computational processing associated with biological sample processing, etc.) such as by facilitating computer performance of functions not previously performable. For example, the technology can apply a set of analytical techniques in a non-generic manner to non-generic microorganism datasets and/or microbiome features (e.g., that are recently able to be generated and/or are viable due to advances in sample processing techniques and/or sequencing technology, etc.) for determining significance index metrics, such as for improving microorganism related characterizations (e.g., diagnoses, etc.) and/or facilitating therapeutic intervention for microorganism-related conditions.

Third, specific examples of the technology can confer improvements in processing speed, microorganism-related characterization, accuracy, microbiome-related therapy determination and promotion, and/or other suitable aspects, such as in relation to microorganism-related conditions. For example, the technology can leverage non-generic microorganism datasets to determine, select, and/or otherwise process microbiome features of particular relevance to one or more types of microorganism-related conditions (e.g., processed microbiome features relevant to a microorganism-related condition; cross-condition microbiome features with relevance to a plurality of microorganism-related conditions, etc.), which can facilitate improvements in accuracy (e.g., by using the most relevant microbiome features; by leveraging tailored analytical techniques; etc.), processing speed (e.g., by selecting a subset of relevant microbiome features; by performing dimensionality reduction techniques; by leveraging tailored analytical techniques; etc.), and/or other computational improvements (e.g., in relation to phenotypic prediction, such as indications of the microorganism-related conditions, etc.), other suitable characterizations, therapeutic intervention facilitation, and/or other suitable purposes. In a specific example, the technology can apply feature-selection rules (e.g., microbiome feature-selection rules for composition, function; for supplemental features extracted from supplementary datasets; etc.) to select an optimized subset of features (e.g., microbiome functional features relevant to one or more microorganism-related conditions; microbiome composition diversity features such as reference relative abundance features indicative of healthy, presence, absence, and/or other suitable ranges of taxonomic groups associated with microorganism related conditions; user relative abundance features that can be compared to reference relative abundance features correlated with microorganism-related conditions and/or therapy responses; etc.) out of a vast potential pool of features (e.g., extractable from the plethora of microbiome data such as sequence data; identifiable by univariate statistical tests; etc.) for generating, applying, and/or otherwise facilitating characterization and/or therapies (e.g., through models, etc.). The potential size of microbiomes (e.g., human microbiomes, animal microbiomes, etc.) can translate into a plethora of data, giving rise to questions of how to process and analyze the vast array of data to generate actionable microbiome insights in relation to microorganism-related characterizations. However, the feature-selection rules and/or other suitable computer-implementable rules can enable one or more of: shorter generation and execution times (e.g., for generating and/or applying models; for determining microorganism-related characterizations and/or associated therapies; etc.); optimized sample processing techniques (e.g., improving transformation of microorganism nucleic acids from biological samples through using primer types, other biomolecules, and/or other sample processing components identified through computational analysis of taxonomic groups, sequences, and/or other suitable data associated with microorganism-related conditions, such as while optimizing for improving specificity, reducing amplification bias, and/or other suitable parameters; etc.); model simplification facilitating efficient interpretation of results; reduction in overfitting; network effects associated with generating, storing, and applying microorganism-related characterizations for a plurality of users over time in relation to microorganism-related conditions (e.g., through collecting and processing an increasing amount of microbiome-related data associated with an increasing number of users to improve predictive power of the microorganism-related characterizations and/or therapy determinations; etc.); improvements in data storage and retrieval (e.g., storing and/or retrieving significance index models; storing specific models such as in association with different users and/or sets of users, with different microorganism-related conditions; storing microorganism datasets in association with user accounts; storing therapy monitoring data in association with one or more therapies and/or users receiving the therapies, such as in relation to significance index metrics; storing features, microorganism-related characterizations, and/or other suitable data in association with a user, set of users, and/or other entities to improve delivery of personalized characterizations and/or treatments for the microorganism-related conditions, etc.), and/or other suitable improvements to technological areas.

Fourth, specific examples of the technology can amount to an inventive distribution of functionality across components including a sample handling system, a microorganism-related characterization system, and a plurality of users, where the sample handling system can handle substantially concurrent processing of biological samples (e.g., in a multiplex manner) from the plurality of users, which can be leveraged by the microorganism-related characterization system in generating personalized characterizations, and/or therapies (e.g., customized to the user's microbiome such as in relation to the user's dietary behavior, probiotics-associated behavior, medical history, demographic characteristics, other behaviors, preferences, etc.) for microorganism-related conditions.

Fifth, specific examples of the technology can improve the technical fields of at least genomics, microbiology, microbiome-related computation, diagnostics, therapeutics, microbiome-related digital medicine, digital medicine generally, modeling, and/or other relevant fields. In an example, the technology can model and/or characterize different microorganism-related conditions, such as through computational identification of relevant microorganism features (e.g., which can act as biomarkers to be used in diagnoses, facilitating therapeutic intervention, etc.) for microorganism-related conditions. In another example, the technology can perform cross-condition analysis to identify and evaluate cross-condition microbiome features associated with (e.g., shared across, correlated across, etc.) a plurality of a microorganism-related conditions (e.g., diseases, phenotypes, etc.). Such identification and characterization of microbiome features can facilitate improved health care practices (e.g., at the population and individual level, such as by facilitating diagnosis and therapeutic intervention, etc.), by reducing risk and prevalence of comorbid and/or multi-morbid microorganism-related conditions (e.g., which can be associated with environmental factors, and thereby associated with the microbiome, etc.). In specific examples, the technology can apply unconventional processes (e.g., sample processing processes; computational analysis processes; etc.), such as to confer improvements in technical fields.

Sixth, the technology can leverage specialized computing devices (e.g., devices associated with the sample handling system, such as next-generation sequencing systems; microorganism-related characterization systems; therapy facilitation systems; etc.) in performing suitable portions associated with embodiments of the method 100 and/or system 200.

Specific examples of the technology can, however, provide any suitable improvements in the context of using non-generalized components and/or suitable components of embodiments of the system 200 for microorganism-related characterization, microbiome modulation, and/or for performing suitable portions of embodiments of the method 100.

4. Other

Embodiments of the method 100 can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

Embodiments of the method 100 and/or system 200 can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with the system. The computer-readable medium can be stored on any suitable computer-readable media such as RAMs, ROMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims.

TABLE 1

| Significance | Samples | | Theoretical | |
|---|---|---|---|---|
| Index Metric/Score | Minimum | Maximum | Minimum | Maximum |
| First example | 1.4 | 87.38 | 0 | 88.43 |
| Second example | 0 | 99.99 | 0 | 99.99 |
| Third example | −40.71 | 45.45 | −41.0 | 64.0 |
| Fourth example | −17.34 | 45.45 | −17.46 | 63.9 |
| Fifth example | −4.59 | 1.42 | −5.10 | 2.38 |
| Sixth example | −4.20 | 0.34 | −5.92 | 2.38 |

TABLE 2

| Taxa | Correlation coefficient | Bayes factor | Probability of association; Calculated with Bayes factor (BF) as probability of association = BF/(1 + BF) |
|---|---|---|---|
| *Fusobacterium nucleatum* | −0.1 | 0.14 | 0.12 |
| *Gardnerella* | 0.083 | 0.42 | 0.29 |
| *Gardnerella vaginalis* | 0.34 | 5.81 | 0.85 |
| *Lactobacillus iners* | −0.41 | 0.74 | 0.42 |
| *Sneathia* | 0.64 | 35453.65 | 0.99 |

We claim:

1. A method for characterizing at least one microorganism-related condition, the method comprising:
   determining a set of associations between a set of microorganism taxa and the at least one microorganism-related condition by automatically processing data sources using natural language processing algorithms to extract the set of microorganism taxa and associated conditions to generate the set of associations, wherein the set of associations comprises at least one of positive associations, negative associations, and non-associations;
   determining a set of reference abundance ranges for the set of microorganism taxa using a machine learning algorithm, wherein the reference abundance ranges are associated with the at least one microorganism-related condition and comprise healthy abundance ranges corresponding to healthy range of relative abundance of the microorganism taxa associated with the at least one microorganism-related condition, and unhealthy abundance ranges corresponding to unhealthy range of relative abundance of the microorganism taxa associated with the at least one microorganism-related condition; and
   determining a significance index metric comprising a propensity score characterizing the set of associations between the set of microorganism taxa and the at least one microorganism-related condition, based on the set of associations and the reference abundance ranges for the set of microorganism taxa,
   wherein the propensity score is indicative of propensity of a user for the at least one microorganism-related condition.

2. The method of claim 1, wherein determining the significance index metric comprises:
   determining effect size metrics for the set of associations between the set of microorganism taxa and the at least one microorganism-related condition, based on the set of reference abundance ranges for the set of microorganism taxa; and
   determining the significance index metric based on the effect size metrics.

3. The method of claim 2,
   wherein determining the effect size metrics comprises determining a set of coefficient of correlations for the set of associations between the set of microorganism taxa and the at least one microorganism-related condition, based on a meta-analysis, and
   wherein determining the significance index metric based on the effect size metrics comprises determining the significance index metric based on the set of coefficient of correlations.

4. The method of claim 2,
   wherein determining the effect size metrics comprises determining a set of z-scores for the set of associations between the set of microorganism taxa and the at least one microorganism-related condition; and
   modifying the set of z-scores based on the reference abundance ranges for the set of microorganism taxa and at least one of the positive associations and the negative associations between the set of microorganism taxa and the at least one microorganism-related condition; and
   wherein determining the significance index metric based on the effect size metrics comprises determining the significance index metric based on the modified set of z-scores.

5. The method of claim 2,
   wherein determining the effect size metrics comprises performing an interpolation process based on the reference abundance ranges and a calibration curve derived from a random set of abundances for the set of microorganism taxa, and
   wherein determining the significance index metric based on the effect size metrics comprises determining the significance index metric based on the interpolation process.

6. The method of claim 2, wherein determining the significance index metric comprises determining a propensity score for a user describing an association between a user microbiome and the at least one microorganism-related condition, based on the effect size metrics and user abundances for the set of microorganism taxa.

7. The method of claim 6, wherein determining the significance index metric comprises normalizing the propensity score based on a set of empirical abundance ranges for the set of microorganism taxa.

8. The method of claim 1, wherein determining the significance index metric comprises:
   determining a set of labels for a user sample, wherein determining the set of labels comprises determining a label of the set of labels for a taxon of the set of microorganism taxa based on satisfaction of an abundance condition by a user abundance for the taxon in relation to a reference abundance range for the taxon, and satisfaction of an association type condition by an association, of the set of associations, between the taxon and the at least one microorganism-related condition, and
   determining the significance index metric for a user associated with the user sample, based on the set of labels.

9. The method of claim 1, wherein determining the significance index metric comprises determining a microorganism-related condition classification associated with a health state of a user for the at least one microorganism-related condition, based on user microbiome composition features and a machine learning model derived from the set of associations and the set of reference abundance ranges.

10. The method of claim 1, further comprising facilitating diagnosis of the user for the at least one microorganism-related condition based on the significance index metric and a user sample comprising microorganisms associated with the set of microorganism taxa.

11. The method of claim 1, further comprising facilitating therapeutic intervention for the user for the at least one microorganism-related condition based on the significance index metric and a user sample comprising microorganisms associated with the set of microorganism taxa.

12. A method for characterizing at least one microorganism-related condition in relation to a user, the method comprising:
collecting a biological sample from a user and supplementary data associated with the user, wherein the biological sample comprises microorganisms associated with the at least one microorganism-related condition;
determining user microbiome composition features associated with the microorganisms, based on the biological sample, wherein the user microbiome composition features comprise user abundance for a set of microorganism taxa;
determining reference microbiome composition features associated with the set of microorganism taxa based a set of reference abundance ranges for the set of microorganism taxa on using a machine learning algorithm, wherein the reference abundance ranges comprise healthy abundance ranges corresponding to healthy range of relative abundance of the microorganism taxa associated with the at least one microorganism-related condition, and unhealthy abundance ranges corresponding to unhealthy range of relative abundance of the microorganism taxa associated with the at least one microorganism-related condition and
determining, for the user, a significance index metric comprising a propensity score for the user characterizing an association between a user microbiome and the at least one microorganism-related condition, based on the user microbiome composition features, effect size metrics determined based on the reference microbiome composition features, and a set of associations between the set of microorganism taxa and the at least one microorganism-related condition,
wherein the propensity score is indicative of propensity of a user for the at least one microorganism-related condition.

13. The method of claim 12, wherein determining the significance index metric for the user comprises determining the significance index metric based on the user microbiome composition features and a set of coefficient of correlations for the set of associations between the set of microorganism taxa and the at least one microorganism-related condition.

14. The method of claim 12, wherein determining the significance index metric for the user comprises determining the significance index metric based on the user microbiome composition features and a set of modified z-scores determined based on the reference microbiome composition features and a set of z-scores for the set of associations between the set of microorganism taxa and the at least one microorganism-related condition.

15. The method of claim 12, wherein determining the significance index metric for the user comprises determining the significance index metric based on the user microbiome composition features and an interpolation process with the reference microbiome composition features and a calibration curve derived from a random set of abundances for the set of microorganism taxa.

16. The method of claim 12, wherein determining the propensity score comprises determining the propensity score based on the user abundances, the effect size metrics, and significance metrics for the effect sizes.

17. The method of claim 12, wherein determining the significance index metric comprises normalizing the propensity score based on a set of empirical abundance ranges for the set of microorganism taxa.

18. The method of claim 12, wherein determining the significance index metric comprises:
determining a set of labels for the sample, wherein determining the set of labels comprises determining a label of the set of labels for a taxon of the set of microorganism taxa based on satisfaction of an abundance condition by a user abundance for the taxon in relation to a reference abundance range for the taxon, and satisfaction of an association type condition by an association, of the set of associations, between the taxon and the at least one microorganism-related condition, and
determining the significance index metric for the user based on the set of labels.

19. The method of claim 12, wherein determining the significance index metric comprises determining a microorganism-related condition classification associated with a health state of the user for the at least one microorganism-related condition, based on the user microbiome composition features and a machine learning model derived from the set of associations and the set of reference microbiome composition features.

20. The method of claim 19, wherein determining the microorganism-related condition classification comprises determining a diet-related condition classification, associated with a diet-related condition, for the user based on the machine learning model and the user microbiome composition features associated with the set of microorganism taxa.

21. The method of claim 20,
wherein the diet-related condition comprises at least one of caffeine consumption, alcohol consumption, artificial sweetener consumption, and sugar consumption;
wherein determining the microorganism-related condition classification comprises determining at least one of a caffeine consumption classification, an alcohol consumption classification, an artificial sweetener consumption classification, and a sugar consumption classification, for the user based on the machine learning model and the user microbiome composition features associated with the set of microorganism taxa,
wherein the set of microorganism taxa comprises at least one of: *Alistipes*; *Anaerotruncus*; *Bacteroides*; *Bifidobacterium*; *Bilophila*; *Blautia*; *Butyricimonas*; *Clostridium*; *Collinsella*; *Erysipelatoclostridium*; *Faecalibacterium*; *Flavobacterium*; *Flavonifractor*; *Granulicatella*; *Hespellia*; *Intestinimonas*; *Kluyvera*; *Lachnospira*; *Marvinbryantia*; *Odoribacter*; *Oscillibacter*; *Parabacteroides*; *Phascolarctobacterium*; *Pseudobutyrivibrio*; *Roseburia*; *Streptococcus*; *Subdoli granulum*; *Sutterella*; and *Terri sporobacter.*

22. The method of claim 12, further comprising facilitating diagnosis of the user for the at least one microorganism-related condition based on the significance index metric.

23. The method of claim 12, further comprising facilitating therapeutic intervention for the user for the at least one microorganism-related condition based on the significance index metric.

* * * * *